US009901639B2

(12) United States Patent
Wang

(10) Patent No.: US 9,901,639 B2
(45) Date of Patent: Feb. 27, 2018

(54) BONE MARROW ORIGIN PROGENITOR CELL OR ENDOTHELIAL PROGENITOR CELL IN COMBINATION WITH DNMT1 GENE THERAPY FOR VASCULAR REPAIR IN METABOLIC DISEASE

(71) Applicant: Temple University—of the Commonwealth System of Higher Education, Philadelphia, PA (US)

(72) Inventor: Hong Wang, Huntingdon Valley, PA (US)

(73) Assignee: Temple University—of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 15/044,859

(22) Filed: Feb. 16, 2016

(65) Prior Publication Data
US 2016/0235789 A1  Aug. 18, 2016

Related U.S. Application Data

(60) Provisional application No. 62/115,979, filed on Feb. 13, 2015.

(51) Int. Cl.
*A01N 63/00* (2006.01)
*A61K 45/06* (2006.01)
*C12N 5/071* (2010.01)
*A61K 48/00* (2006.01)
*A61K 35/28* (2015.01)

(52) U.S. Cl.
CPC .............. *A61K 45/06* (2013.01); *A61K 35/28* (2013.01); *A61K 48/00* (2013.01); *C12N 5/0692* (2013.01)

(58) Field of Classification Search
None
See application file for complete search history.

(56) References Cited

U.S. PATENT DOCUMENTS

| | | |
|---|---|---|
| 5,501,979 A | 3/1996 | Geller et al. |
| 5,561,063 A | 10/1996 | Hock et al. |
| 5,576,201 A | 11/1996 | Mason et al. |
| 5,604,090 A | 2/1997 | Alexander et al. |
| 5,624,820 A | 4/1997 | Cooper et al. |
| 5,665,577 A | 9/1997 | Sodroski et al. |
| 5,674,703 A | 10/1997 | Woo et al. |
| 5,693,508 A | 12/1997 | Chang et al. |
| 5,700,470 A | 12/1997 | Saito et al. |
| 5,719,054 A | 2/1998 | Boursnell et al. |
| 5,731,172 A | 3/1998 | Saito et al. |
| 5,928,944 A | 7/1999 | Seth et al. |
| 6,013,516 A | 1/2000 | Verma et al. |
| 2010/0119490 A1* | 5/2010 | Yoon ............ C12N 5/0647 424/93.7 |

FOREIGN PATENT DOCUMENTS

| | | |
|---|---|---|
| WO | 92/05266 A2 | 4/1992 |
| WO | 92/14829 A1 | 9/1992 |

OTHER PUBLICATIONS

Zhang et al., "Severe Hyperhomocysteinemia Promotes Bone Marrow-Derived and Resident Inflammatory Monocyte Differentiation and Atherosclerosis in LDLr/CBS-Deficient Mice", Circulation research, 111:37-49, 2012.
Tan et al., "Hyperhomocysteinemia inhibits post-injury reendothelialization in mice", Cardiovascular research, 69:253-262, 2006.
Jamaluddin et al., "Homocysteine inhibits endothelial cell growth via DNAhypomethylation of the cylin A gene", Blood, 110(10):3648-3655, 2007.
Jiang et al., "Hyperhomocystinemia Impairs Endothelial Function and eNOS Activity via PKC Activation", Arteriosclerosis thrombosis and vascular biology, 25:2515-2521, 2005.
Wang et al., "Hyperhomocysteinemia accelerates atherosclerosis in cystathionine Beta-synthase and apolipoprotein E double knock-out mice with and without dietary perturbation", Blood, 101:3901-3907, 2003.
Liao et al., "Hyperhomocysteinemia Decreases Circulating High-Density Lipoprotein by Inhibiting Apolipoprotein A-I Protein Synthesis and Enhancing HDL Cholesterol Clearance", Circulation research, 99:598-606, 2006.
Cheng et al., "Hyperhomocysteinemia impairs endothelium-derived hyperpolarizing factor-mediated vasorelaxation in transgenic cystathionine beta synthase-deficient mice", Blood, 118:1998-2006.
Kawamoto et al., "Intramyocardial Transplantation of Autologous Endothelial Progenitor Cells for Therapeutic Neovascularization of Myocardial Ischemia",Circulation, 107:461-468, 2003.
Chen et al., "Effects of homocysteine on number and activity of endothelial progenitor cells from peripheral blood", Journal of molecular and cellular cardiology, 36:233-239, 2004.
Werner et al., "Circulating Endothelial Progenitor Cells and Cardiovascular Outcomes", N. Engl J Med, 353:999-1007, 2005.
Mano et al., "Dietary intervention with Okinawan vegetables increased circulating endothelial progenitor cells in healthy young women", Atherosclerosis, 204:544-548, 2009.
Jourde-Chiche et al., "Levels of circulating endothelial progenitor cells are related to uremic toxins and vascular injury in hemodialysis patients", J Thromb Haemost, 7:1576-1584, 2009.
Alam et al., "Homocysteine reduces endothelial progenitor cells in stroke patients through apoptosis", J Cereb Blood Flow Metab, 29:157-165, 2009.
Bogdanski et al., "Plasma total homocysteine is a determinant of carotid intima-media thickness and circulating endothelial progenitor cells in patients with newly diagnosed hypertension", Clinical chemistry and laboratory medicine, 50:1107-1113, 2012.

(Continued)

Primary Examiner — Michael Burkhart
(74) Attorney, Agent, or Firm — Riverside Law LLP

(57) ABSTRACT

The present invention provides an isolated population of bone marrow-derived endothelial progenitor cells (EPCs) and uses thereof for the treatment of vascular diseases.

10 Claims, 8 Drawing Sheets

(56) References Cited

OTHER PUBLICATIONS

Delva et al., "Endothelial progenitor cells in patients with essential hypertension", Journal of hypertension, 25:127-132, 2007.

Jourde-Chiche et al., "Vascular Incompetence in Dialysis Patients—Protein-Bound Uremic Toxins and Endothelial Dysfunction", Seminars in dialysis, 24:327-337, 2011.

Huang et al., "Enodthelial progenitor cells are associated with plasma homocysteine in coronary artery diesease", Acta cardiologica, 66:773-777, 2011.

Cone et al., "High-efficiency gene transfer into mammalian cells: Generation of helper-free recombinant retrovirus with broad mammalian host range", Proc. Natl. Acad. Sci. USA, 81:6349-6353, 1984.

Sarver et al., "Bovine Papilloma Virus Deoxyribonucleic Acid: a Novel Eucaryotic Cloning Vector", Mol. Cell. Biol, 1:486-496, 1981.

Watanabe et al., "Mice deficient in cystathionine Beta-synthase: Animal models for mild and severe homocyst(e) inemia", Proc. Natl. Acad. Sci. USA, 92:1585-1589, 1995.

Wu et al., "Cleaved high molecular weight kininogen inhibits tube formation of endothelial progenitor cells via suppression of matrix metalloproteinase 2", J Thromb Haemost, 8:185-193, 2010.

Wang et al., "Prevention of Sympathetic and Cardiac Dysfunction After Myocardial Infarction in Transgenic Rats Deficient in Brain Angiotensinogen", Circulation research, 94:843-849, 2004.

Stellos et al., "Expression of stromal-cell-derived factor-1 on circulating platelets is increased in patients with acute aoronary syndrome and correlates with the number of CD34+ progenitor cells", Eur Heart J, 30:584-593, 2009.

Kokubo et al., "Integrin Alpha v Beta 3 as a target in the prevention of neointimal hyperplasia", Journal of vascular surgery, A:A33-38, 2007.

Walter et al., "Stalin Therapy Accelerates Reendothelialization A Novel Effect Involving Mobilization and Incorporation of Bone Marrow-Derived Endothelial Progenitor Cells", Circulation, 105:3017-3024, 2002.

McIlhenny et al., "Linear Shear Conditioning Improves Vascular Graft Retention of Adipose-Derived Stem Cells by Upregulation of the alpha 5 beta 1 Integrin", Tissue Eng Part A, vol. 15, No. 00:pp. 1-11 (2009).

Ohle et al., "Maintenance and Repair of the Lung Endothelium Does Not Involve Contributions from Marrow-Derived Endothelial Precursor Cells", Am J Respir Cell Mol Biol, 47:11-19, 2012.

Duan et al., "LFA-1 and VLA-4 involved in human high proliferative potential-endothelial progenitor cells homing to ischemic tissue", Thromb Haemost, 96:807-815, 2006.

de Boer et al., "Fibrin and Activated Platelets Cooperatively Guide Stem Cells to a Vascular Injury and Promote Differentiation Towards an Endothelial Cell Phenotype", Arteriosclerosis, thrombosis, and vascular biology, 26:1653-1659, 2006.

Korta et al., "Stem and progenitor cells in biostructure of blood vessel walls", Postepy Hig Med Dosw, 67:982-995, 2013.

Koch et al., "Capillary endothelia and cardiomyocytes differ in vulnerability to ischemia/reperfusion during clinical heart transplantation", European journal of cardio-thoracic surgery, 20:996-1001, 2001.

Wang et al., "HyperhomoGysteinemia accelerates atherosclerosis in cystathionine beta-synthase and apolipoprotein E double knock-out mice with and without dietary perturbation", Blood, 99:939-945, 2002.

Wang et al., "Inhibition of Growth and p21ras Methylation in Vascular Endothelial Cells by Homocysteine but Not Cysteine", The Journal of biological chemistry, 272:25380-25385, 1997.

Yang, J et al., "CD34+ Cells Represent Highly Functional Endothelial Progenitor Cells in Murine Bone Marrow", PloS one, 6:e20219, 2011.

Kalka et al., "Transplantation of ex vivo expanded endothelial progenitor cells for therapeutic neovascularization", Proceedings of the National Academy of Sciences of the United States of America, 97:3422-3427, 2000.

Hohenstein et al., "Autocrine VEGF-VEGF-R loop on podocytes during glomerulonephritis in humans", Nephrology, dialysis, transplantation, 25:3170-3180, 2010.

Nakajima et al., "Presenilin-1 controls the growth and differentiation of endothelial progenitor cells through its Beta-catenin-binding region", Cell Biol Int, 30:239-243, 2006.

Patschan et al., "Dynamics of mobilization and homing of endothelial progenitor cells after acute renal ischemia: modulation by ischemic preconditioning", American journal of physiology. Renal physiology, 291:F176-F185, 2006.

Heeschen et al., "Erythropoietin is a potent physiologic stimulus for endothelial progenitor cell mobilization", Blood, 102:1340-1346, 2003.

Carmeliet et al., "Vascular Wound Healing and Neointima Formation Induced by Perivascular Electric Injury in Mice", The American journal of pathology, 150:761-776, 1997.

Iwakura et al., "Estrogen-Mediated, Endothelial Nitric Oxide Synthase-Dependent Mobilization of Bone Marrow-Derived Endothelial Progenitor Cells Contributes to Reendothelialization After Arterial Injury", Circulation, 108:3115-3121, 2003.

* cited by examiner

BONE MARROW ORIGIN PROGENITOR CELL OR ENDOTHELIAL PROGENITOR CELL IN COMBINATION WITH DNMT1 GENE THERAPY FOR VASCULAR REPAIR IN METABOLIC DISEASE

CROSS-REFERENCES TO RELATED APPLICATIONS

This application claims priority to U.S. Provisional Patent Application No. 62/115,979 filed on Feb. 13, 2015, the contents of which are incorporated by reference herein in its entirety.

STATEMENT REGARDING FEDERALLY SPONSORED RESEARCH OR DEVELOPMENT

This invention was made with government support under grant numbers HL67033, HL77288, HL82774, HL110764, HL117654, HL9445, HL108910, and HL116917 awarded by the National Institutes of Health (NIH). The government has certain rights in the invention.

BACKGROUND OF THE INVENTION

Hyperhomocysteinemia (HHcy) has been recognized as a potent risk factor for cardiovascular disease (CVD). Several biological mechanisms have been suggested to explain cardiovascular pathological changes associated with HHcy. It has been reported that HHcy accelerates atherosclerosis by inhibiting endothelial cell (EC) growth, post-injury re-endothelialization, endothelial-dependent vessel relaxation and HDL biosynthesis (Zhang, D et al., Circulation research, 2012; 111:37-49; Tan, H et al., Cardiovascular research, 2006; 69:253-262; Jamaluddin, M D et al., Blood, 2007; 110:3648-3655; Jiang, X et al., Arteriosclerosis, thrombosis, and vascular biology, 2005; 25:2515-2521; Wang, H et al., Blood, 2003; 101:3901-3907; Liao, D et al., Circulation research, 2006; 99:598-606; and Cheng, Z et al., Blood, 118:1998-2006). It has also been reported that HHcy impairs re-endothelialization and promotes post-injury neointimal formation via inhibiting EC proliferation and migration (Tan, H et al., Cardiovascular research, 2006; 69:253-262).

It is known that bone marrow (BM)-derived endothelial progenitor cells (EPCs) can enter the circulation, home to the injured endothelium and ischemic myocardium, and participate in re-endothelialization (Kawamoto, A et al., Circulation, 2003; 107:461-468 and Chen, J Z et al., Journal of molecular and cellular cardiology, 2004; 36:233-239). Circulating EPC population can be identified as CD34$^+$ alone, CD34$^+$/VEGFR2$^+$, or CD34$^+$/CD31$^+$, which is decreased in patients with atherosclerosis, stroke, and hemodialysis (Werner, N et al., N Engl J Med., 2005; 353:999-1007; Mano, R et al., Atherosclerosis, 2009; 204:544-548; Jourde-Chiche, N et al., J Thromb Haemost, 2009; 7:1576-1584; and Alam, M M et al., J Cereb Blood Flow Metab, 2009; 29:157-165). The Framingham study (Werner, N et al., N Engl J Med., 2005; 353:999-1007) showed that circulating EPCs is associated with cardiovascular risk scores, a clinical index for 10-year risk of developing coronary heart disease (CHD) based on age, total cholesterol level, HDL cholesterol level, smoke and systolic blood pressure. Decreased EPC population is associated with carotid intima-media thickness and flow-mediated vascular dilation in hypertensive patients (Bogdanski, P et al., Clinical chemistry and laboratory medicine: CCLM/FESCC, 2012; 50:1107-1113 and Delva, P et al., Journal of hypertension, 2007; 25:127-132) and associated with endothelial dysfunction in dialysis patients with chronic kidney disease (CKD) (Jourde-Chiche, N et al., J Thromb Haemost, 2009; 7:1576-1584 and Jourde-Chiche, N et al., Seminars in dialysis, 2011; 24:327-337). It was reported that elevated plasma levels of Hcy reduced circulating EPC counts in patients with CHD (Huang, C et al., Acta cardiologica, 2011; 66:773-777). However, the effect of HHcy on EPC generation and its impact on vascular injury has not been studied. The mechanism underlying HHcy-impaired EPC function is unknown.

Since EPCs were first described more than a decade ago, many groups focused especially on its regenerative potential and tried to unravel their unique properties and characteristics with the ultimate goal to improve the clinical applicability and efficacy of these cells in the fight against CVD. Although extensive work has been conducted to verify if EPC impairment plays a key role in coronary atherogenesis (Kawamoto, A et al., Circulation, 2003; 107:461-468), it remains unclear if these cells exert favorable or unfavorable effects at sites of percutaneous coronary intervention (PCI) due to discordant definitions of EPCs and different timing of EPC sampling (Kawamoto, A et al., Circulation, 2003; 107:461-468; Chen, J Z et al., Journal of molecular and cellular cardiology, 2004; 36:233-239; and Werner, N et al., N Engl J Med., 2005; 353:999-1007). In addition, development of de novo lesions and post-PCI restenosis are pathophysiologically dissimilar. The role of EPCs in restenosis progression needs to be examined concomitantly and serially over time.

There is a need in the art for vascular repair therapies in subjects with metabolic disorders. The present invention addresses this unmet need.

SUMMARY OF THE INVENTION

In one aspect, the present invention provides a method of treating a vascular disease in a subject, comprising administering to a subject in need thereof an effective amount of bone marrow-derived endothelial progenitor cells (EPCs) to the subject. In one embodiment, the vascular disease is associated with endothelial injury. In one embodiment, the vascular disease is hyperhomocysteinemia (HHcy), hyperlipidemia, or diabetes associated vascular injury.

In one embodiment, the bone marrow-derived EPCs are CD34$^+$/VEGFR2$^+$.

In one embodiment, the method further comprises modifying the bone marrow-derived EPCs by gene transfer. In one embodiment, the gene is DNMT1.

In one embodiment, the bone marrow-derived EPCs are modified prior to administration to the subject. In one embodiment, the bone marrow-derived EPCs are modified during or after administration to the subject.

In one embodiment, the bone marrow-derived EPCs are administered to the subject by direct injection, venous infusion, or arterial infusion. In one embodiment, the bone marrow-derived EPCs differentiate into endothelial cells in the subject.

In one embodiment, the subject is also treated, either serially or in parallel, with a combination therapy. In one embodiment, the combination therapy comprises administering to the subject at least one active agent selected from a therapeutic agent, an anti-angiogenic or anti-vascular agent, an anti-inflammation agent, a VEGF inhibitor, an antibiotic, an anti-viral agent, an anti-fungal agent, an anti-protozoal agents, a hormone, a radioactive agent, a toxin, an anesthetic, or any combinations thereof.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A. Serum levels of Hcy. Hcy levels were measured using a Biochrom 30 amino acid analyzer. FIG. 1B. Representative FSC-SSC dot plot depicting MNCs. MNCs are gated in gate i excluding neutrophils, red blood cells, platelets, and cell fragments. FIG. 1C. Representative percentage of $CD34^+/VEGFR2^+$ progenitor cells. Dot plot shows $CD34^+/VEGFR2^+$ progenitor cells in quadrant 2 (R2) from MNCs (gate i). FIG. 1D. Quantitative analysis of $CD34^+/VEGFR2^+$ progenitor cells. FIG. 1E. Correlation of Hcy levels with $CD34^+/VEGFR2^+$ progenitor cells in BM. Each data point represents one mouse. Values present mean±SD. n=10; *, P<0.05 vs mice on CT diet in the same transfusion group. Hcy, homocysteine; CT, control; HM, high methionine; Tx, transfusion; BM, bone marrow; PB, peripheral blood; FSC, forward-scatter light; SSC, side-scatter light; MNC, mononuclear cell.

FIG. 2, comprising FIG. 2A. Schematic description of experimental strategy. FIG. 2B. Gross appearance of injured carotid artery. A suture was placed to mark the air-exit hole at the proximal end of the common carotid artery. The injured segment is about 5 mm from the bifurcation of the carotid artery to the air-exit hole. FIG. 2C. Representative images of Evans Blue staining of injured carotids. Blue stained area depicts nonviable endothelial zone. The area of endothelial denudation is defined as the bifurcation of carotid artery to the suture. FIG. 2D. Quantitative analysis of re-endothelialization. Re-endothelialization was examined in $Cbs^{-/+}$ mice with CT or HM diet from day 0 to day 9 post-injury. FIG. 2E. Correlation analysis of Hcy levels with re-endothelialization area. Each data point represents 1 mouse. F. Representative percentage of $CD34^+/VEGFR2^+$ progenitor cells. Dot plot shows $CD34^+/VEGFR2^+$ progenitor cells in quadrant 2 (R2) from MNCs (gate i) (as described in FIG. 1B) in PB of Cbs mice at the indicated times. FIG. 2G. Quantitative analysis of $CD34^+/VEGFR2^+$ progenitor cells. $CD34^+/VEGFR2^+$ progenitor cells were examined and quantified. Values represent mean±SD. n=6; *, P<0.05 vs mice on control diet at the same time point. Post-op, post operation; CT, control; HM, high methionine; PB, peripheral blood; MNC, mononuclear cell.

FIG. 3, comprising FIG. 3A. Schematic description of experimental strategy. FIG. 3B. Representative percentage of $GFP^+$ cells in PB of donor and recipient mice. BM $GFP^+CD34^+$ cell were adoptively transferred into recipient $Cbs^{-/+}$ mice. Mouse blood was collected 30 min after adoptively transfer and analyzed by flow cytometry for $GFP^+$ and $GFP^-$ frequency measurement. FIG. 3C. Representative percentage of $GFP^-$ and $GFP^+CD34^+/VEGFR2^+$ progenitor cells. MNCs were gated as described in FIG. 1B in the peripheral blood from $Cbs^{-/+}$ mice 0.5 h after surgery and BM $GFP^+CD34^+$ cell transfusion. Dot plots showed $GFP^+$ and $GFP^-CD34^+/VEGFR2^+$ progenitor cells in quadrant 2 (R2) from MNCs in PB pre-injury and indicated time points post-injury with BM $CD34^+$ transfusion from EGFP transgenic mice. D. Quantitative analysis of $CD34^+/VEGFR2^+$ progenitor cells. $GFP^+$ and $GFP^-$ $CD34^+/VEGFR2^+$ progenitor cells were examined in PB of Cbs mice pre-injury and 0.5 h, 1 d, 3 d, and 6 d post-injury with BM $CD34^+$ transfusion from EGFP transgenic mice. Values are mean±SD. n=6. *, P<0.05 vs mice on CT diet at 0.5 h time point. #, P<0.05 vs mice on HM diet at 0.5 h time point. $, P<0.05 vs mice on CT diet at the same time point. CT, control; HM, high methionine; Tx, transfusion. MNC, mononuclear cell.

FIG. 4, comprising FIG. 4A. Schematic description of experimental strategy. FIG. 4B. Representative in vivo images of $CD34^+$ cells homing to the injured carotid artery. Transfused $CD34^+$ cells labeled with IRDye800CW dye were imaged prior to or at 30 min, 90 min, 24 h, 48 h, and 72 h post $CD34^+$ cells Tx. Images showed $CD34^+$ cells accumulated at the site of the injured carotid 24 h post-Tx and continued afterwards. FIG. 4C. Representative images of re-endothelialization and GFP $CD34^+$ homing on the injured carotid artery. Re-endothelialization and homing of transfused $CD34^+$ cells was assessed by en face staining with antibody against CD31 (endothelial marker) and anti-GFP antibodies on 7 days post-injury. FIG. 4D. Quantitative analysis of $GFP^+CD34^+$ cells on injured carotid artery. FIG. 4E. Quantitative analysis of re-endothelialization after carotid artery injury with $CD34^+$ cells transfusion. FIG. 4F. Representative images of $CD34^+$ incorporated in neointima. Longitude-sections of injured carotid were stained with antibody against CD31 (endothelial marker) and anti-GFP antibodies 14 days after carotid injury. FIG. 4G. Representative images of neointima on injured carotid artery. The neointima was defined as the region between the lumen and internal elastic lamina. FIG. 4H. Quantitative analysis of vascular remodeling. FIG. 4I. Correlation analysis of Hcy levels with vascular remodeling. Each data point represents 1 mouse. Values are mean±SD. n=6; *, P<0.05 vs mice on CT diet with saline Tx. #, P<0.05 vs mice on CT diet with CD34+ cells Tx, ¶, P<0.05 vs mice on HM diet with saline Tx; CT, control; HM, high methionine; Tx, transfusion.

FIG. 5, comprising FIG. 5A. Representative images of hEPC characterization. hEPCs exhibited cobblestone-like morphology, showing positive staining for acLDL (red) and ulex-lectin (green) after incubation with acLDL (5 µg/ml, 1 h). FIG. 5B. Representative images of hEPC adhesion. hEPCs treated with L-Hcy for 48 h were harvested and plated on fibronectin-coated cell culture plates for 1 hour at 37° C. Attached cells were photographed and quantified in high-power fields under an inverted microscope. FIG. 5C. Quantitative analysis of adhesion. FIG. 5D. Representative images of hEPC migration. Confluent hEPCs were incubated with L-Hcy for 48 h, scratched to create a wound and evaluated for migration after 20 h. E. Quantitative analysis of migration. FIG. 5F. Quantitative analysis of hEPC proliferation. 80% confluent hEPCs were treated with L-Hcy for 24 h and labeled with $^3$[H]-thymidine for the last 4 h. Incorporated $^3$[H]-thymidine was measured in a liquid scintillation counter. FIG. 5G. Quantitative analysis of hEPC viability. Confluent hEPCs were treated with L-Hcy for 48 h and nuclear counts determined by crystal violet staining to determine the viable cells. Data are representative of 3 separate experiments and are shown as mean±SD. *P<0.05 versus control. hEPCs; human endothelial progenitor cells; Hcy, homocysteine.

FIG. 6, comprising FIG. 6A. Representative FSC-SSC dot plots for live cells selection. Live cells were selected in gate i and analyzed for integrin expression and activity. FIG. 6B. Representative histograms of basal β1 and αvβ3 integrin. HUVECs were used as an endothelial lineage positive control. Confluent hEPCs and HUVECs were harvested for β1 or αvβ3 surface expression. FIG. 6C. Representative histograms of β1 and αvβ3 integrin in hEPCs. Confluent hEPCs were incubated with L-Hcy (250 µmol/L) for 48 hours and harvested with trypsin for β1 or αvβ3 surface expression. FIG. 6D. Quantitative analysis of β1 and αvβ3 integrin. E. Representative histogram of β1 integrin activity. hEPCs treated with L-Hcy for 48 hours were harvested and incubated with HUTS21 antibody of β1 integrin for β1 activity assessment. FIG. 6F. Quantitative analysis of β1 integrin activity. G. Quantitative analysis of adhesion rescue. hEPCs were incubated with L-Hcy (250 µmol/L) in the presence of antibody 12G10 (β1 integrin function-activating antibody) or isotype IgG for 48 h and plated on fibronectin-coated cell culture plate for adhesion assay. FIG. 6H. Quantitative analysis of migration rescue. Confluent hEPCs were incubated with L-Hcy in the presence of antibody 12G10 or isotype IgG for 24 h, scratched to create a wound and evaluated for migration in the presence of antibody 12G10 after 20 h. Data are representative of 3 separate experiments and are shown as mean±SD. *, P<0.05 vs control; #, P<0.05 vs isotype IgG control; hEPC, human endothelial progenitor cells; Hcy, homocysteine.

FIG. 7, comprising FIG. 7A. Body weight. FIG. 7B through FIG. 7F. Heart, lung, liver, kidney, and spleen weights relative to tibia lengths, respectively. Values are presented as mean±SD. n=10; *, P<0.05 versus CBS$^{-/+}$ mice on CT diet in the presence and absence of CD34+ progenitor cells transfusion; Hcy, homocysteine; CT, control; HM, high methionine; BW, body weight; BM, bone marrow; PB, peripheral blood; FSC, forward-scatter light; SSC, side-scatter light; Tx, transfusion; MNC, mononuclear cell.

DETAILED DESCRIPTION

Figures 1A, 1B, 1C, 1D, 1E:
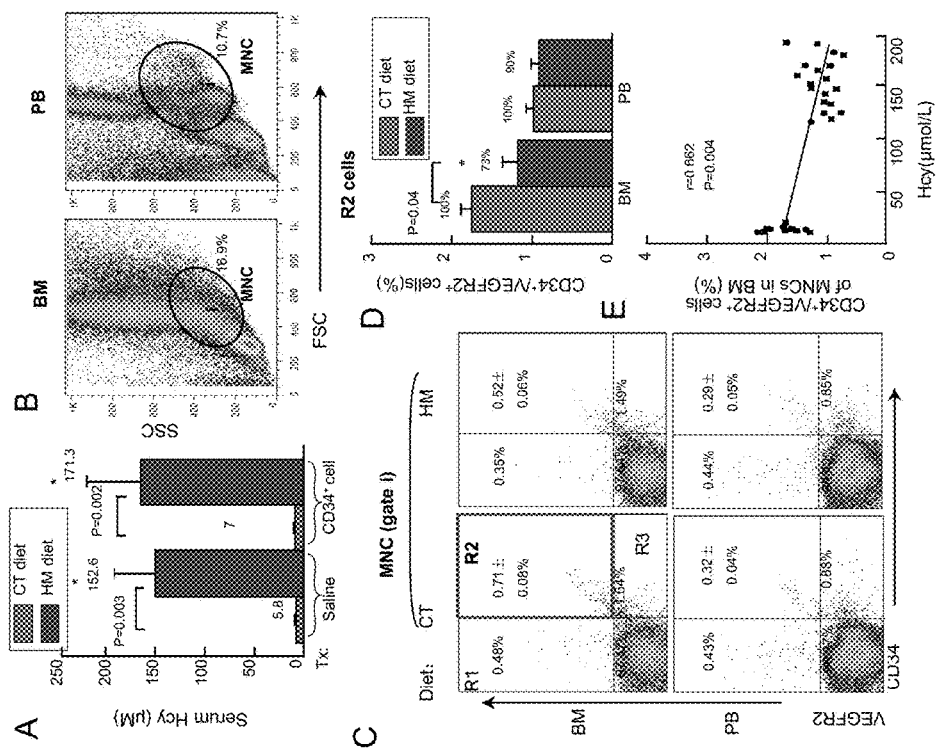
FIG. 1A through FIG. 1E, depicts the results of experiments demonstrating that HHcy reduces $CD34^+/VEGFR2^+$ progenitor cells in the BM. Severe HHcy was developed in $Cbs^{-/+}$ mice fed a HM diet at 8 weeks of age for an additional 8 weeks. BM $CD34^+$ cells were isolated from EGFP transgenic mice and immediately transfused into $Cbs^{-/+}$ mice with control or HM diet after air-dry carotid artery injury. Peripheral blood and BM cells were collected at the end of the experiment, stained with antibodies against CD34 and VEGFR2, and analyzed by flow cytometry.

The present invention provides compositions and methods of using bone marrow (BM)-derived progenitor cells (PCs) in the treatment of a vascular disease. In one embodiment, the vascular disease is associated with endothelial injury, such as hyperhomocysteinemia (HHcy) associated vascular injury. In one embodiment, the bone marrow (BM)-derived progenitor cells (PCs) comprise bone marrow (BM)-derived endothelial progenitor cells (EPCs).

In one embodiment, the invention provides the use of BM-derived progenitor cells in combination with DNMT1 gene therapy for vascular repair in a metabolic disorders, such as HHcy, hyperlipidemia and diabetes, in which EPC suppression, endothelial injury, and hypomethylation metabolic changes were observed.

This invention further encompasses a composition of substantially purified population of PCs, wherein the EPCs are CD34+/VEGFR2+.

This invention further encompasses a method of isolating a population of bone marrow-derived PCs, comprising isolating cells from a subject, and purifying cells that are CD34+ by antibody coated magnetic beads purification.

The invention is based partly on the discovery that (1) severe HHcy suppresses progenitor cell (PC) generation in the bone marrow and inhibits its post-injury mobilization; (2) HHcy reduces PC homing and contribution to endothelial regeneration; (3) transfusion of BM-derived PCs improves re-endothelialization and reduces neointimal formation in Cbs deficient mice; (4) Hcy inhibits human EPC migration and adhesion via β1 integrin reduction/inactivation. (5) Hyperlipidemia and diabetes also suppress EPC, and cause endothelial injury and hypomethylation metabolic changes.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

As used herein, "a cell that differentiates into a mesodermal (or ectodermal or endodermal) lineage" defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoetic, hemangiogenic, myogenic, nephrogenic, urogenitogenic, osteogenic, pericardiogenic, or stromal. Examples of cells that differentiate into ectodermal lineage include, but are not limited to epidermal cells, neurogenic cells, and neurogliagenic cells. Examples of cells that differentiate into endodermal lineage include, but are not limited to pleurigenic cells, and hepatogenic cells, cell that give rise to the lining of the intestine, and cells that give rise to pancreogenic and splanchogenic cells.

As used herein "conditioned media" defines a medium in which a specific cell or population of cells have been cultured in, and then removed. While the cells were cultured in said medium, they secrete cellular factors that include, but are not limited to hormones, cytokines, extracellular matrix (ECM), proteins, vesicles, antibodies, and granules. The medium plus the cellular factors is the conditioned medium.

The term "dedifferentiation", as used herein, refers to the return of a cell to a less specialized state. After dedifferentiation, such a cell will have the capacity to differentiate into more or different cell types than was possible prior to re-programming. The process of reverse differentiation (i.e., de-differentiation) is likely more complicated than differentiation and requires "re-programming" the cell to become more primitive.

"Differentiated" is used herein to refer to a cell that has achieved a terminal state of maturation such that the cell has developed fully and demonstrates biological specialization and/or adaptation to a specific environment and/or function. Typically, a differentiated cell is characterized by expression of genes that encode differentiation associated proteins in that cell. When a cell is said to be "differentiating," as that term is used herein, the cell is in the process of being differentiated.

"Differentiation medium" is used herein to refer to a cell growth medium comprising an additive or a lack of an additive such that a stem cell, adipose derived adult stromal cell or other such progenitor cell, that is not fully differentiated when incubated in the medium, develops into a cell with some or all of the characteristics of a differentiated cell.

The term "derived from" is used herein to mean to originate from a specified source.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

"Expandability" is used herein to refer to the capacity of a cell to proliferate, for example, to expand in number or in the case of a cell population to undergo population doublings.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

As used herein "growth factors" is intended the following non-limiting factors including, but not limited to, growth hormone, erythropoietin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor (EGF), fibroblast growth factor (FGF), nerve growth factor, ciliary neurotrophic factor, platelet derived growth factor (PDGF), transforming growth factor (TGF-beta), hepatocyte growth factor (HGF), and bone morphogenetic protein at concentrations of between picogram/ml to milligram/ml levels.

As used herein, the term "growth medium" is meant to refer to a culture medium that promotes growth of cells. A growth medium will generally contain animal serum. In some instances, the growth medium may not contain animal serum.

An "isolated cell" refers to a cell which has been separated from other components and/or cells which naturally accompany the isolated cell in a tissue or mammal.

As used herein, the "lineage" of a cell defines the heredity of the cell, i.e.; which cells it came from and what cells it can give rise to. The lineage of a cell places the cell within a hereditary scheme of development and differentiation.

A "multi-lineage stem cell" or "multipotent stem cell" refers to a stem cell that reproduces itself and at least two further differentiated progeny cells from distinct developmental lineages. The lineages can be from the same germ layer (i.e. mesoderm, ectoderm or endoderm), or from different germ layers. An example of two progeny cells with distinct developmental lineages from differentiation of a multi-lineage stem cell is a myogenic cell and an adipogenic cell (both are of mesodermal origin, yet give rise to different tissues). Another example is a neurogenic cell (of ectodermal origin) and adipogenic cell (of mesodermal origin).

As used herein, a "passage" refers to a round of subculturing. Thus, when cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but, not limited to, the seeding density, substrate, medium, and time between passaging.

As used herein, a "pluripotent cell" defines a less differentiated cell that can give rise to at least two distinct (genotypically and/or phenotypically) further differentiated progeny cells.

The terms "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew itself or to produce progeny cells which will differentiate into the desired cell type. Unlike pluripotent stem cells, lineage-committed progenitor cells are generally considered to be incapable of giving rise to numerous cell types that phenotypically differ from each other. Instead, progenitor cells give rise to one or possibly two lineage-committed cell types.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

"Progression of or through the cell cycle" is used herein to refer to the process by which a cell prepares for and/or enters mitosis and/or meiosis. Progression through the cell cycle includes progression through the G1 phase, the S phase, the G2 phase, and the M-phase.

A cell of the present invention may be characterized as "positive" for a particular biomarker. A cell positive for a biomarker is one wherein a cell of the invention expresses a specific biomarker protein, or a nucleic acid encoding said protein.

A cell of the present invention may be characterized as "negative" for a particular biomarker. A cell negative for a biomarker is one wherein a cell of the invention does not express a detectable specific biomarker protein, or a nucleic acid encoding said protein.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, a cell exists in a "purified form" when it has been isolated away from all other cells that exist in its native environment, but also when the proportion of that cell in a mixture of cells is greater than would be found in its native environment. Stated another way, a cell is considered to be in "purified form" when the population of cells in question represents an enriched population of the cell of interest, even if other cells and cell types are also present in the enriched population. A cell can be considered in purified form when it comprises in some embodiments at least about 10% of a mixed population of cells, in some embodiments at least about 20% of a mixed population of cells, in some embodiments at least about 25% of a mixed population of cells, in some embodiments at least about 30% of a mixed population of cells, in some embodiments at least about 40% of a mixed population of cells, in some embodiments at least about 50% of a mixed population of cells, in some embodiments at least about 60% of a mixed population of cells, in some embodiments at least about 70% of a mixed population of cells, in some embodiments at least about 75% of a mixed population of cells, in some embodiments at least about 80% of a mixed population of cells, in some embodiments at least about 90% of a mixed population of cells, in some embodiments at least about 95% of a mixed population of cells, and in some embodiments about 100% of a mixed population of cells, with the proviso that the cell comprises a greater percentage of the total cell population in the "purified" population that it did in the population prior to the purification. In this respect, the terms "purified" and "enriched" can be considered synonymous.

"Self-renewal" refers to the ability to produce replicate daughter stem cells having differentiation potential that is identical to those from which they arose. A similar term used in this context is "proliferation."

As used herein, "stem cell" defines an undifferentiated cell that can produce itself and a further differentiated progeny cell.

As used herein, "tissue engineering" refers to the process of generating tissues ex vivo for use in tissue replacement or reconstruction. Tissue engineering is an example of "regenerative medicine," which encompasses approaches to the repair or replacement of tissues and organs by incorporation of cells, gene or other biological building blocks, along with bioengineered materials and technologies.

As used herein, a "vascular disease" refers to a disease of the vessels, primarily arteries and veins, which transport blood to and from the heart, brain and peripheral organs such as, without limitation, the arms, legs, kidneys and liver. In particular "vascular disease" refers to the coronary arterial and venous systems, the carotid arterial and venous systems, the aortic arterial and venous systems and the peripheral arterial and venous systems. The disease that may be treated is any that is amenable to treatment with a therapeutic agent, either as the sole treatment protocol or as an adjunct to other procedures such as surgical intervention. The disease may be, without limitation, atherosclerosis, vulnerable plaque, restenosis or peripheral arterial disease. Peripheral vascular disease includes arterial and venous diseases of the renal, iliac, femoral, popliteal, tibial and other vascular regions.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to isolated bone marrow-derived EPCs and cells derived therefrom and methods of using such cells in any application including but is not limited to the treatment of vascular diseases.

In one embodiment, the invention provides the use of BM-derived endothelial progenitor cells in combination with DNMT1 gene therapy for vascular repair in metabolic disorder.

In one embodiment, the cells of the invention can be combined with Hcy-lowering strategy or gene-therapy with the correction of targeting genes identified in Hcy signaling as a method for treating a vascular disease.

Some prominent conditions that fall under the category of "vascular diseases" are e.g. peripheral vascular disease, aneurysm, renal artery disease, Raynaud's phenomenon (also called Raynaud's disease or Raynaud's syndrome), Buerger's disease, peripheral venous disease, varicose veins, venous blood clots, deep vein thrombosis (DVT), pulmonary embolism, chronic venous insufficiency, and other vascular conditions such as e.g., blood clotting disorders, lymphedema, vein graft disease, etc.

Vascular diseases may also comprise aneurysms. An aneurysm is usually an abnormal bulge in the wall of a blood vessel. Such aneurysms can form in any blood vessel, but occur most commonly in the aorta (aortic aneurysm) which is the main blood vessel leaving the heart, e.g. the thoracic aortic aneurysm (part of aorta in the chest), the abdominal aortic aneurysm, including suprarenal aneurysm (involving the arteries above the kidneys), juxtarenal aneurysm (involving the main renal arteries), and infrarenal aneurysm (involving the arteries below the kidneys). There is an increased risk of atherosclerotic plaque (fat and calcium deposits) formation at the site of the aneurysm, clot (thrombus) formation and shedding at the site of the aneurysm, but the most severe cases increase in size and may lead to rupture.

Renal artery disease is most commonly caused by atherosclerosis of the renal arteries (see above). It occurs in people with generalized vascular disease. Less often, renal artery disease can be caused by fibromuscular dysplasia, a congenital (present at birth) abnormal development of the tissue that makes up the renal arteries. This type of renal artery disease occurs in younger age groups.

Two further prominent vascular diseases known in the above context are Raynaud's phenomenon (also called Raynaud's disease or Raynaud's syndrome) and Buerger's disease. Raynaud's phenomenon consists of spasms of the small arteries of the fingers, and sometimes, the toes, brought on by exposure to cold or excitement. Certain occupational exposures bring on Raynaud's phenomenon. The episodes produce temporary lack of blood supply to the area, causing the skin to appear white or bluish and cold or numb. In some cases, the symptoms of Raynaud's phenomenon may be related to underlying connective tissue disorders (i.e., lupus, rheumatoid arthritis, scleroderma). Buerger's disease most commonly affects the small and medium sized arteries, veins, and nerves. Although the trigger and the mechanism are unknown, there is a strong association with tobacco use or exposure. The arteries of the arms and legs become narrowed or blocked, causing lack of blood supply (ischemia) to the fingers, hands, toes and feet. Pain occurs in the arms, hands, and more frequently the legs and feet, even at rest. With severe blockages, the tissue may die (gangrene), requiring amputation of the fingers and toes. Superficial vein inflammation and symptoms of Raynaud's phenomenon occur commonly in patients with Buerger's Disease.

Vascular diseases can also comprise peripheral diseases, such as peripheral vascular disease (PVD), commonly referred to as peripheral arterial disease (PAD) or peripheral artery occlusive disease (PAOD), which refers to the obstruction of large arteries not within the coronary, aortic arch vasculature, or brain. PVD can result from atherosclerosis, inflammatory processes leading to stenosis, an embolism, or thrombus formation, the build-up of fat and cholesterol deposits, called plaque, on the inside walls of peripheral arteries (blood vessels outside the heart). Over time, the build-up narrows the artery and may eventually lead to an obstructed blood flow. Diminished amounts of oxygen and nutrients reaching the target organ due to lack of blood flow in the body's tissue typically lead to ischemia (acute or chronic ischemia). A blockage in the carotid arteries (the arteries supplying the brain) can additionally lead to a transient ischemic attack (TIA) or stroke. A blockage in the legs can lead to leg pain or cramps with activity (claudication), changes in skin color, sores or ulcers and feeling tired in the legs. Total loss of circulation can lead to gangrene and loss of a limb. Finally, a blockage in the renal arteries can cause renal artery disease (stenosis). The symptoms include uncontrolled hypertension (high blood pressure), congestive heart failure, and abnormal kidney function. PAD is a term used to refer to atherosclerotic blockages found in the lower extremity.

Another peripheral disease in the context of vascular diseases is the so called peripheral venous disease. Veins are flexible, hollow tubes with flaps inside, called valves. When muscles contract, the valves open, and blood moves through the veins. When muscles relax, the valves close, keeping blood flowing in one direction through the veins. However, if the valves inside the veins become damaged, the valves may not close completely. This allows blood to flow in both directions. When muscles relax, the valves inside the damaged vein(s) will not be able to hold the blood, causing the pooling of blood or swelling in the veins, that is a typical effect of peripheral venous disease. The blood begins to move more slowly through the veins and it may stick to the sides of the vessel walls and blood clots can form. Peripheral venous disease may also lead to so called varicose veins. Varicose veins are bulging, swollen, purple, ropy veins, seen just under the skin, caused by damaged valves within the veins. There are many further vascular diseases, which may be identified in this context.

Bone Marrow-Derived Endothelial Progenitor Cells

The invention provides bone marrow-derived endothelial progenitor cells (also referred sometimes herein as bone marrow-derived EPC). An EPC cell is an undifferentiated cell that can be induced to proliferate using the methods of the present invention. The EPC is capable of self-maintenance, such that with each cell division, at least one daughter cell will also be an EPC cell. EPCs are capable of being expanded 100, 250, 500, 1000, 2000, 3000, 4000, 5000 or more fold.

Phenotyping of EPCs reveals that these cells express the committed hematopoietic marker CD45. Additionally, an EPC is immunoreactive for VEGFR-2. The EPC is a multipotent progenitor cell. By multipotent progenitor cell is meant that the cell is capable of differentiating into more than one cell type. For example, the cell is capable of differentiating into an endothelial cell or a smooth muscle cell.

Vascular endothelial growth factor (VEGF) acts through specific tyrosine kinase receptors that includes VEGFR-1 (flt-1) and VEGFR-2 (flk-1/KDR) and VEGFR-3/Flt-4 which convey signals that are essential for embryonic angiogenesis and hematopoiesis. While VEGF binds to all three receptors, most biological functions are mediated via VEGFR-2 and the role of VEGFR-1 is currently unknown. VEGFR3/Flt4 signaling is known to be important for the development of lymphatic endothelial cells and VEGFR3 signaling may confer lymphatic endothelial-like phenotypes to endothelial cells. VEGFRs relay signals for processes essential in stimulation of vessel growth, vasorelaxation, induction of vascular permeability, endothelial cell migration, proliferation and survival. Endothelial cells express all different VEGF-Rs. During embryogenesis, it has been reported that a single progenitor cell, the hemangioblast can give rise to both the hematopoietic and vascular systems.

Bone marrow can be used as a source of the bone marrow-derived EPCs of the invention. The cells isolated from bone marrow can be introduced into a subject for tissue regeneration, wound repair or other applications requiring a source of EPCs. The bone marrow-derived EPCs can also be cultured in vitro to maintain a source of EPCs, or can be induced to produce further differentiated EPCs that can develop into a desired tissue.

The cells of the invention can be obtained by mechanically and enzymatically dissociating cells from bone marrow. Mechanical dissociation can be brought about using methods that include, without limitation, chopping and/or mincing the tissue, and/or centrifugation and the like. Enzymatic dissociation of connective tissue and from cell-to-cell associations can be brought about by enzymes including, but not limited to, Blendzyme, DNAse I, collegenase and trypsin, or a cocktail of enzymes found to be effective in liberating cells from the bone marrow sample. The procedure for mechanically and enzymatically isolating a cell of the present invention should not be construed to be limited to the materials and techniques presented herein, but rather it will be recognized that these techniques are well-established and fall well within the scope of experimental optimization performed routinely in the art.

The bone marrow-derived EPCs of the invention are isolated from bone marrow. In the isolation of the cells of the invention, bone marrow can be obtained from any animal by any suitable method. A first step in any such method requires the isolation of bone marrow from the source animal. The animal can be alive or dead, so long as cells within bone marrow are viable. Typically, human bone marrow is obtained from a living donor, using well-recognized surgical protocols. The cells of the invention are present in the initially excised or extracted bone marrow, regardless of the method by which bone marrow is obtained. In another embodiment, bone marrow may be obtained from non-human animals.

In one embodiment, a bone marrow is removed from the animal. In one embodiment, bone marrow is washed with a physiologically-compatible solution, such as phosphate buffer saline (PBS). The washing step consists of rinsing bone marrow with PBS, agitating the tissue, and allowing the tissue to settle. In one embodiment, bone marrow is dissociated. The dissociation can occur by enzyme degradation and neutralization. Alternatively, or in conjunction with such enzymatic treatment, other dissociation methods can be used such as mechanical agitation, sonic energy, or thermal energy.

In some instances, it may be desirable to further process the dissociated tissue. For example, the dissociated bone marrow can be filtered to isolate cells from other connective tissue. The extracted cells can be concentrated into a pellet. One method to concentrate the cells includes centrifugation, wherein the sample is centrifuged and the pellet retained. The pellet includes the bone marrow-derived EPCs of the invention.

In one embodiment, the cells are resuspended and can be washed (e.g. in PBS). Cells can be centrifuged and resuspended successive times to achieve a greater purity. In one embodiment, the cells extracted from bone marrow may be a heterogeneous population of cell which includes the bone marrow-derived EPCs of the invention. bone marrow-derived EPCs may be separated from other cells by methods that include, but are not limited to, cell sorting, size fractionation, granularity, density, molecularity, morphologically, and immunohistologically. In one embodiment, bone marrow-derived EPCs of the invention are separated from other cells by assaying the length of the telomere, as stem cells tend to have longer telomeres compared to differentiated cells. In another embodiment, bone marrow-derived EPCs of the invention are separated from other cells by assaying telomeric activity, as telomeric activity can serve as a stem-cell specific marker. In another embodiment, bone marrow-derived endothelial cells of the invention are separated from other cells immunohistochemically, for example, by panning, using magnetic beads, or affinity chromatography.

The bone marrow-derived EPCs can be cultured and, if desired, assayed for number and viability, to assess the yield. In one embodiment, the stem cells are cultured without differentiation using standard cell culture media (e.g., DMEM, typically supplemented with 5-15% (e.g., 10%) serum (e.g., fetal bovine serum, horse serum, etc.). In one embodiment, the stem cells are passaged at least five times in such medium without differentiating, while still retaining their developmental phenotype. In one embodiment, the stem cells are passaged at least 10 times (e.g., at least 15 times or even at least 20 times) while retaining potency.

The bone marrow-derived EPCs can be separated by phenotypic identification, to identify those cells that have two or more of the aforementioned developmental lineages. In one embodiment, all cells extracted from bone marrow are cultured. To phenotypically separate the bone marrow-derived EPCs from the other cells of bone marrow, the cells are plated at a desired density, such as between about 100 cells/cm$^2$ to about 100,000 cells/cm$^2$ (such as about 500 cells/cm$^2$ to about 50,000 cells/cm$^2$, or, more particularly, between about 1,000 cells/cm$^2$ to about 20,000 cells/cm$^2$).

In one embodiment the extracted cells of bone marrow is plated at a lower density (e.g., about 300 cells/cm$^2$) to facilitate the clonal isolation of the bone marrow-derived EPCs. For example, after a few days, bone marrow-derived EPCs plated at such densities will proliferate (expand) into a clonal population of bone marrow-derived EPCs.

Such bone marrow-derived EPCs can be used to clone and expand a clonal population, using a suitable method for cloning cell populations. The cloning and expanding methods include cultures of cells, or small aggregates of cells, physically picking and seeding into a separate plate (such as the well of a multi-well plate). Alternatively, the stem cells can be subcloned onto a multi-well plate at a statistical ratio for facilitating placing a single cell into each well (e.g., from about 0.1 to about 1 cell/well or even about 0.25 to about 0.5 cells/well, such as 0.5 cells/well). The bone marrow-derived EPCs can be cloned by plating them at low density (e.g., in a petri-dish or other suitable substrate) and isolating them from other cells using devices such as a cloning rings. Alternatively, where an irradiation source is available, clones can be obtained by permitting the cells to grow into a monolayer and then shielding one and irradiating the rest of cells within the monolayer. The surviving cell then will grow into a clonal population. Production of a clonal population can be expanded in any suitable culture medium, for example, an exemplary culture condition for cloning stem cells (such as the inventive stem cells or other stem cells) is about ⅔ F12 medium+20% serum (e.g. fetal bovine serum) and about ⅓ standard medium that has been conditioned with stromal cells, the relative proportions being determined volumetrically).

In any event, whether clonal or not, the isolated bone marrow-derived EPCs can be cultured in a specific inducing medium to induce the bone marrow-derived EPCs to differentiate and express its potency. The bone marrow-derived EPCs give rise to cells of mesodermal, ectodermal and endodermal lineage, and combinations thereof. Thus, bone marrow-derived EPCs can be treated to differentiate into a variety of cell types.

The bone marrow-derived EPCs of the invention can be induced to differentiate into a mesodermal, ectodermal, or an endodermal lineage by co-culturing the cells of the invention with mature cells from the respective germ layer, or precursors thereof.

Alternatively, the bone marrow-derived EPCs are cultured in a conditioned medium and induced to differentiate into a specific phenotype. Conditioned medium is medium which was cultured with a mature cell that provides cellular factors to the medium such as cytokines, growth factors, hormones, and extracellular matrix. For example, a medium that has been exposed to mature myocytes is used to culture and induce bone marrow-derived EPCs to differentiate into a myogenic lineage. Other examples of conditioned media inducing specific differentiation include, but are not limited to, culturing in a medium conditioned by exposure to heart valve cells to induce differentiation into heart valve tissue.

For co-culture, it may be desirable for the bone marrow-derived EPCs and the desired other cells to be co-cultured under conditions in which the two cell types are in contact. This can be achieved, for example, by seeding the cells as a heterogeneous population of cells onto a suitable culture substrate. Alternatively, the bone marrow-derived EPCs can first be grown to confluence, which will serve as a substrate for the second desired cells to be cultured within the conditioned medium.

Other methods of inducing differentiation are known in the art and can be employed to induce the bone marrow-derived EPCs to give rise to cells having a mesodermal, ectodermal or endodermal lineage.

After culturing the stem cells of the invention in the differentiating-inducing medium for a suitable time (e.g., several days to a week or more), the bone marrow-derived EPCs can be assayed to determine whether, in fact, they have acquired the desired lineage.

Methods to characterize differentiated cells that develop from the bone marrow-derived EPCs of the invention, include, but are not limited to, histological, morphological, biochemical and immunohistochemical methods, or using cell surface markers, or genetically or molecularly, or by identifying factors secreted by the differentiated cell, and by the inductive qualities of the differentiated bone marrow-derived EPCs.

In another embodiment, a population of bone marrow-derived EPCs can support cells for culturing other cells. For example, cells that can be supported by bone marrow-derived EPCs populations include other types of stem cells, such as neural stem cells (NSC), hematopoietic stem cells (HPC, particularly CD34+ stem cells), embryonic stem cells (ESC) and mixtures thereof), osteoblasts, neurons, chondrocytes, myocytes, and precursors thereof. In other embodiments, the population is substantially homogeneous, consisting essentially of the inventive bone marrow-derived EPCs.

In one embodiment, the bone marrow-derived EPCs of the invention are capable of vascular repair. In another embodiment, the bone marrow-derived EPCs of the invention are capable of angiogenesis. Accordingly, the bone marrow-derived EPCs of the present invention can be used to treat vascular tissue damaged due to injury or disease. It is understood by those of skill in the art that the term treating, as used herein, includes repairing, replacing, augmenting, improving, rescuing, repopulating, or regenerating.

It may be desirable to induce differentiation of the bone marrow-derived EPCs of the invention in a controlled manner and/or by employing factors which are not easily or desirably introduced into the damaged vascular tissue. Therefore, in one embodiment of the invention, the bone marrow-derived EPCs of the invention can be induced to differentiate prior to being introduced into the recipient by, for example, in vitro exposure to extracellular and/or intracellular factors such as trophic factors, cytokines, mitogens, hormones, cognate receptors for the foregoing, and the like. In another embodiment, the bone marrow-derived EPCs of the invention are not induced to differentiate, but are introduced into the recipient as a substantially pure population of cells that may differentiate following introduction into the recipient.

In one embodiment of the present invention, the bone marrow-derived EPCs of the present invention is autologous. That is, a cell of the invention is procured from a donor and returned to the same individual after selection and expansion of said cell; i.e. donor and recipient are the same individual. In another embodiment of the present invention, the bone marrow-derived EPCs of the present invention are allogenic. That is, the bone marrow-derived EPCs of the invention are procured from a donor but administered to a different individual after selection and expansion of said cell; i.e. the donor and recipient are genetically different individuals.

In one embodiment, the bone marrow-derived EPCs of the invention are capable of vascular repair. In one embodiment, the bone morrow-derived EPCs contribute to post-injury progenitor cell replenishment under normal conditions. In one embodiment, the cells of the invention are capable of homing to the site of vascular injury, and facilitating re-endothelialization and preventing neointimal formation. Accordingly, the cells of the present invention can be used to treat vascular tissue damaged due to injury or disease.

Genetic Modification

In one embodiment, the cells of the invention can be combined with Hcy-lowering strategy or gene-therapy with the correction of targeting genes identified in Hcy signaling as a method for treating a vascular disease.

In one embodiment, the invention provides the use of BM-derived endothelial progenitor cells in combination with DNMT1 gene therapy for vascular repair in metabolic disorder.

In another embodiment, the bone marrow-derived EPCs can be genetically modified, e.g., to express exogenous (e.g., introduced) genes ("transgenes") or to repress the expression of endogenous genes, and the invention provides a method of genetically modifying such cells and populations. Preferably, the cells of the invention are genetically modified to express DNMT1. In accordance with this method, the bone marrow-derived EPCs is exposed to a gene transfer vector comprising a nucleic acid including a transgene, such that the nucleic acid is introduced into the cell under conditions appropriate for the transgene to be expressed within the cell. The transgene generally is an expression cassette, including a polynucleotide operably linked to a suitable promoter. The polynucleotide can encode a protein, or it can encode biologically active RNA (e.g., antisense RNA or a ribozyme). Of course, where it is desired to employ gene transfer technology to deliver a given transgene, its sequence will be known.

In the context of gene therapy, the cells of the invention can be treated with a gene of interest prior to delivery of the cells into the recipient. In some cases, such cell-based gene delivery can present significant advantages of other means of gene delivery, such as direct injection of an adenoviral gene delivery vector. Delivery of a therapeutic gene that has been pre-inserted into cells avoids the problems associated with penetration of gene therapy vectors into desired cells in the recipient.

Accordingly, the invention provides the use of genetically modified cells that have been cultured according to the methods of the invention. Genetic modification may, for instance, result in the expression of exogenous genes ("transgenes") or in a change of expression of an endogenous gene. Such genetic modification may have therapeutic benefit. Alternatively, the genetic modification may provide a means to track or identify the cells so-modified, for instance, after implantation of a composition of the invention into an individual. Tracking a cell may include tracking migration, assimilation and survival of a transplanted genetically-modified cell. Genetic modification may also include at least a second gene. A second gene may encode, for instance, a selectable antibiotic-resistance gene or another selectable marker.

The cells of the invention may be genetically modified using any method known to the skilled artisan. See, for instance, Sambrook et al. (2001, Molecular Cloning: A Laboratory Manual, Cold Spring Harbor Laboratory Press, Cold Spring Harbor, N.Y.). For example, a cell may be exposed to an expression vector comprising a nucleic acid including a transgene, such that the nucleic acid is introduced into the cell under conditions appropriate for the transgene to be expressed within the cell. The transgene generally is an expression cassette, including a polynucleotide operably linked to a suitable promoter. The polynucleotide can encode a protein, or it can encode biologically active RNA (e.g., antisense RNA or a ribozyme). Thus, for example, the polynucleotide can encode a gene conferring resistance to a toxin, a hormone (such as peptide growth hormones, hormone releasing factors, sex hormones, adrenocorticotrophic hormones, cytokines (e.g., interferins, interleukins, lymphokines), etc.), a cell-surface-bound intracellular signaling moiety (e.g., cell adhesion molecules, hormone receptors, etc.), a factor promoting a given lineage of differentiation (e.g., bone morphogenic protein (BMP)), etc., and insulin.

Nucleic acids can be of various lengths. Nucleic acid lengths typically range from about 20 nucleotides to 20 Kb, or any numerical value or range within or encompassing such lengths, 10 nucleotides to 10 Kb, 1 to 5 Kb or less, 1000 to about 500 nucleotides or less in length. Nucleic acids can also be shorter, for example, 100 to about 500 nucleotides, or from about 12 to 25, 25 to 50, 50 to 100, 100 to 250, or about 250 to 500 nucleotides in length, or any numerical value or range or value within or encompassing such lengths. Shorter polynucleotides are commonly referred to as "oligonucleotides" or "probes" of single- or double-stranded DNA.

Nucleic acids can be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to antibody encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as yeast or bacteria, a eukaryote such as an animal or mammalian cell or in a plant).

Nucleic acids can be included within vectors as cell transfection typically employs a vector. The term "vector," refers to, e.g., a plasmid, virus, such as a viral vector, or other vehicle known in the art that can be manipulated by insertion or incorporation of a polynucleotide, for genetic manipulation (i.e., "cloning vectors"), or can be used to transcribe or translate the inserted polynucleotide (i.e., "expression vectors"). Such vectors are useful for introducing polynucleotides in operable linkage with a nucleic acid, and expressing the transcribed encoded protein in cells in vitro, ex vivo or in vivo.

A vector generally contains at least an origin of replication for propagation in a cell. Control elements, including expression control elements, present within a vector, are included to facilitate transcription and translation. The term "control element" is intended to include, at a minimum, one or more components whose presence can influence expression, and can include components other than or in addition to promoters or enhancers, for example, leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of a gene of interest, stop codons, among others.

Vectors included are those based on viral vectors, such as retroviral (lentivirus for infecting dividing as well as non-dividing cells), foamy viruses (U.S. Pat. Nos. 5,624,820, 5,693,508, 5,665,577, 6,013,516 and 5,674,703; WO92/05266 and WO92/14829), adenovirus (U.S. Pat. Nos. 5,700,470, 5,731,172 and 5,928,944), adeno-associated virus (AAV) (U.S. Pat. No. 5,604,090), herpes simplex virus vectors (U.S. Pat. No. 5,501,979), cytomegalovirus (CMV) based vectors (U.S. Pat. No. 5,561,063), reovirus, rotavirus genomes, simian virus 40 (SV40) or papilloma virus (Cone et al., Proc. Natl. Acad. Sci. USA 81:6349 (1984); Eukaryotic Viral Vectors, Cold Spring Harbor Laboratory, Gluzman ed., 1982; Sarver et al., Mol. Cell. Biol. 1:486 (1981); U.S.

Pat. No. 5,719,054). Adenovirus efficiently infects slowly replicating and/or terminally differentiated cells and can be used to target slowly replicating and/or terminally differentiated cells. Simian virus 40 (SV40) and bovine papilloma virus (BPV) have the ability to replicate as extra-chromosomal elements (Eukaryotic Viral Vectors, Cold Spring Harbor Laboratory, Gluzman ed., 1982; Sarver et al., Mol. Cell. Biol. 1:486 (1981)). Additional viral vectors useful for expression include reovirus, parvovirus, Norwalk virus, coronaviruses, paramyxo- and rhabdoviruses, togavirus (e.g., sindbis virus and semliki forest virus) and vesicular stomatitis virus (VSV) for introducing and directing expression of a polynucleotide or transgene in pluripotent stem cells or progeny thereof (e.g., differentiated cells).

Vectors including a nucleic acid can be expressed when the nucleic acid is operably linked to an expression control element. As used herein, the term "operably linked" refers to a physical or a functional relationship between the elements referred to that permit them to operate in their intended fashion. Thus, an expression control element "operably linked" to a nucleic acid means that the control element modulates nucleic acid transcription and as appropriate, translation of the transcript.

The term "expression control element" refers to nucleic acid that influences expression of an operably linked nucleic acid. Promoters and enhancers are particular non-limiting examples of expression control elements. A "promoter sequence" is a DNA regulatory region capable of initiating transcription of a downstream (3' direction) sequence. The promoter sequence includes nucleotides that facilitate transcription initiation. Enhancers also regulate gene expression, but can function at a distance from the transcription start site of the gene to which it is operably linked. Enhancers function at either 5' or 3' ends of the gene, as well as within the gene (e.g., in introns or coding sequences). Additional expression control elements include leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of interest, and stop codons.

Expression control elements include "constitutive" elements in which transcription of an operably linked nucleic acid occurs without the presence of a signal or stimuli. For expression in mammalian cells, constitutive promoters of viral or other origins may be used. For example, SV40, or viral long terminal repeats (LTRs) and the like, or inducible promoters derived from the genome of mammalian cells (e.g., metallothionein IIA promoter; heat shock promoter, steroid/thyroid hormone/retinoic acid response elements) or from mammalian viruses (e.g., the adenovirus late promoter; mouse mammary tumor virus LTR) are used.

Expression control elements that confer expression in response to a signal or stimuli, which either increase or decrease expression of operably linked nucleic acid, are "regulatable." A regulatable element that increases expression of operably linked nucleic acid in response to a signal or stimuli is referred to as an "inducible element." A regulatable element that decreases expression of the operably linked nucleic acid in response to a signal or stimuli is referred to as a "repressible element" (i.e., the signal decreases expression; when the signal is removed or absent, expression is increased).

Expression control elements include elements active in a particular tissue or cell type, referred to as "tissue-specific expression control elements." Tissue-specific expression control elements are typically more active in specific cell or tissue types because they are recognized by transcriptional activator proteins, or other transcription regulators active in the specific cell or tissue type, as compared to other cell or tissue types.

In accordance with the invention, there are provided bone marrow-derived EPCs and their progeny transfected with a nucleic acid or vector. Such transfected cells include but are not limited to a primary cell isolate, populations or pluralities of pluripotent stem cells, cell cultures (e.g., passaged, established or immortalized cell line), as well as progeny cells thereof (e.g., a progeny of a transfected cell that is clonal with respect to the parent cell, or has acquired a marker or other characteristic of differentiation).

The nucleic acid or protein can be stably or transiently transfected (expressed) in the cell and progeny thereof. The cell(s) can be propagated and the introduced nucleic acid transcribed and protein expressed. A progeny of a transfected cell may not be identical to the parent cell, since there may be mutations that occur during replication.

Viral and non-viral vector means of delivery into bone marrow-derived EPCs, in vitro, in vivo and ex vivo are included. Introduction of compositions (e.g., nucleic acid and protein) into the cells can be carried out by methods known in the art, such as osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly (methylmethacrolate) microcapsules, respectively, or in a colloid system. Colloidal dispersion systems include macromolecule complexes, nano-capsules, microspheres, beads, and lipid-based systems, including oil-in-water emulsions, micelles, mixed micelles, and liposomes.

Liposomes for introducing various compositions into cells are known in the art and include, for example, phosphatidylcholine, phosphatidylserine, lipofectin and DOTAP (e.g., U.S. Pat. Nos. 4,844,904, 5,000,959, 4,863,740, and 4,975,282; and GIBCO-BRL, Gaithersburg, Md.). Piperazine based amphilic cationic lipids useful for gene therapy also are known (see, e.g., U.S. Pat. No. 5,861,397). Cationic lipid systems also are known (see, e.g., U.S. Pat. No. 5,459,127). Polymeric substances, microcapsules and colloidal dispersion systems such as liposomes are collectively referred to herein as "vesicles."

Therapy

In one embodiment, the bone marrow-derived EPCs of the invention are capable of vascular repair. In one embodiment, the bone morrow-derived EPCs contribute to post-injury progenitor cell replenishment under normal conditions. In one embodiment, the cells of the invention are capable of homing to the site of vascular injury, and facilitating re-endothelialization and preventing neointimal formation. Accordingly, the cells of the present invention can be used to treat vascular tissue damaged due to injury or disease. It is understood by those of skill in the art that the term treating, as used herein, includes repairing, replacing, augmenting, improving, rescuing, repopulating, or regenerating.

In one embodiment, the vascular disease is a cardiovascular disease and/or disorder including but is not limited to, diseases and/or disorders of the pericardium (i.e., pericardium), heart valves (i.e., incompetent valves, stenosed valves, rheumatic heart disease, mitral valve prolapse, aortic regurgitation), myocardium (coronary artery disease, myocardial infarction, heart failure, ischemic heart disease, angina) blood vessels (i.e., arteriosclerosis, aneurysm) or veins (i.e., varicose veins, hemorrhoids). In specific embodiments, the cardiovascular disease includes, but is not limited to, coronary artery diseases (i.e., arteriosclerosis, atherosclerosis, and other diseases of the arteries, arterioles and capillaries or related complaint), acute myocardial infarct, organizing myocardial infarct, ischemic heart disease, arrhythmia, left ventricular dilatation, emboli, heart failure, congestive heart failure, subendocardial fibrosis, left or right ventricular hypertrophy, and myocarditis. Yet further, one skilled in the art recognizes that cardiovascular diseases and/or disorders can result from congenital defects, genetic defects, environmental influences (i.e., dietary influences, lifestyle, stress, etc.), and other defects or influences.

In one embodiment of the present invention, the bone marrow-derived EPCs provides a source endothelial repair progenitors as a cellular agent for vascular therapy. As a source of endothelial repair progenitors and based on in vitro, ex vivo and in vivo studies, the present invention utilizes autologous or allogeneic ex vivo-expanded bone marrow-derived EPCs.

In one example though non-limiting embodiment, the injection (implant via catheter or direct injection) of a mixture of autologous or allogeneic bone marrow-derived EPCs represents an effective and enduring $CD34^+$ progenitor cell replacement therapy. In one embodiment, bone marrow-derived EPCs are not immunologically rejective, and, thus, do not need to come from the patient's bone tissue, but can instead come from a suitable human donor.

In one embodiment, the bone marrow-derived EPCs of the invention can be used to treat vascular diseases and disorders. Bone marrow-derived EPCs of the invention have several properties that can contribute to reducing and/or minimizing damage and promoting vascular repair and regeneration following damage. These include, among other things, the ability to synthesize and secrete growth factors stimulating new blood vessel formation, the ability to synthesize and secrete growth factors stimulating cell survival and proliferation, the ability to proliferate and differentiate into cells directly participating in new blood vessel formation, the ability to engraft damaged myocardium and inhibit scar formation (collagen deposition and cross-linking), and the ability to proliferate and differentiate into endothelial cells.

The cells may also be applied with additives to enhance, control, or otherwise direct the intended therapeutic effect. For example, in one embodiment, and as described herein, the cells may be further purified by use of antibody-mediated positive and/or negative cell selection to enrich the cell population to increase efficacy, reduce morbidity, or to facilitate ease of the procedure. Similarly, cells may be applied with a biocompatible matrix which facilitates in vivo tissue engineering by supporting and/or directing the fate of the implanted cells. In the same way, cells may be administered following genetic manipulation such that they express gene products that are believed to or are intended to promote the therapeutic response(s) provided by the cells.

In accordance with one method, a composition containing bone marrow-derived EPCs of the invention is introduced into the vascular tissue or a desired site in the subject. In brief, this method can be performed as follows. Bone marrow-derived EPCs of the invention are isolated from bone marrow. Once isolated, the bone marrow-derived EPCs of the invention can be purified and/or expanded. The isolated bone marrow-derived EPCs of the invention can then be formulated as a composition comprising the bone marrow-derived EPCs of the invention along with, for example, a pharmaceutically acceptable carrier or adjuvant. The composition so formed can then be introduced into the vascular tissue of a subject. The subject will usually have been diagnosed as having, or being at risk for, a vascular condition, disease, or disorder. Introduction of the composition can be according to methods generally known to the art. For example, the bone marrow-derived EPC composition can be administered to a subject's heart by way of direct injection delivery or catheter delivery. Introduction of bone marrow-derived EPCs can be a single occurrence or can occur sequentially over a period of time selected by the attending physician. The time course and number of occurrences of bone marrow-derived EPC implantation into a subject's vascular system can be dictated by monitoring generation and/or regeneration of vascular tissue, where such methods of assessment of treatment course is within the skill of the art of an attending physician.

It should be recognized that methods of this invention can easily be practiced in conjunction with existing vascular therapies to effectively treat or prevent disease. The methods, compositions, and devices of the invention can include concurrent or sequential treatment with non-biologic and/or biologic drugs.

The subject receiving vascular implantation of bone marrow-derived EPCs according to the methods described herein will usually have been diagnosed as having, or being at risk for, a vascular condition, disease, or disorder. The methods of the invention can be useful to alleviate the symptoms of a variety of disorders, such as disorders associated with aberrant cell/tissue damage, ischemic disorders, and reperfusion related disorders. For example, the methods are useful in alleviating a symptom of myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy. The condition, disease, or disorder can be diagnosed and/or monitored, typically by a physician using standard methodologies. Alleviation of one or more symptoms of the condition, disease, or disorder indicates that the composition confers a clinical benefit, such as a reduction in one or more of the following symptoms: shortness of breath, fluid retention, headaches, dizzy spells, chest pain, left shoulder or arm pain, and ventricular dysfunction.

As disclosed elsewhere herein, bone marrow-derived EPCs may be applied by several routes including systemic administration by venous or arterial infusion (including retrograde flow infusion) or by direct injection into the heart. Systemic administration, particularly by peripheral venous access, has the advantage of being minimally invasive relying on the natural perfusion of the heart and the ability of the bone marrow-derived EPCs to target the site of damage. Cells may be injected in a single bolus, through a slow infusion, or through a staggered series of applications separated by several hours or, provided cells are appropriately stored, several days or weeks. Cells may also be applied by use of catheterization such that the first pass of cells through the heart is enhanced by using balloons to manage myocardial blood flow. As with peripheral venous access, cells may be injected through the catheters in a single bolus or in multiple smaller aliquots. Cells may also be applied directly to the myocardium by epicardial injection. This could be employed under direct visualization in the context of an open heart procedure (such as a Coronary Artery Bypass Graft Surgery) or placement of a ventricular assist device. Catheters equipped with needles may be employed to deliver cells directly into the myocardium in an endocardial fashion which would allow a less invasive means of direct application.

In one embodiment, the route of delivery includes intravenous delivery through a standard peripheral intravenous catheter, a central venous catheter, or a pulmonary artery catheter. In other embodiments, the cells may be delivered through an intracoronary route to be accessed via currently accepted methods. The flow of cells may be controlled by serial inflation/deflation of distal and proximal balloons located within the patient's vasculature, thereby creating temporary no-flow zones which promote cellular engraftment or cellular therapeutic action. In another embodiment, cells may be delivered through an endocardial (inner surface of heart chamber) method which may require the use of a compatible catheter as well as the ability to image or detect the intended target tissue. Alternatively, cells may be delivered through an epicardial (outer surface of the heart) method. This delivery may be achieved through direct visualization at the time of an open heart procedure or through a thoracoscopic approach requiring specialized cell delivery instruments. Furthermore, cells could be delivered through the following routes, alone, or in combination with one or more of the approaches identified above: subcutaneous, intramuscular, sublingual, retrograde coronary perfusion, coronary bypass machinery, extracorporeal membrane oxygenation (ECMO) equipment and via a pericardial window.

In one embodiment, cells are administered to the patient as an intra-vessel bolus or timed infusion. In another embodiment, cells may be resuspended in an artificial or natural medium or tissue scaffold prior to be administered to the patient.

In one embodiment, the effects of cell delivery therapy would be demonstrated by, but not limited to, one of the following clinical measures: increased heart ejection fraction, decreased rate of heart failure, decreased infarct size, decreased associated morbidity (pulmonary edema, renal failure, arrhythmias) improved exercise tolerance or other quality of life measures, and decreased mortality. The effects of cellular therapy can be evident over the course of days to weeks after the procedure. However, beneficial effects may be observed as early as several hours after the procedure, and may persist for several years.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Hyperhomocysteinemia Inhibits $CD34^+/VEGFR2^+$ Progenitor Cell Mobilization and Homing in Post-Injury Vascular Repair in Mice and Suppresses β1 Integrin in Human Endothelial Progenitor Cells The results presented herein are based on the application of endothelial progenitor cells (EPCs) on vascular remodeling. EPCs were characterized and the therapeutic potential of progenitor cells (PCs) in hyperhomocysteinemia (HHcy) was evaluated. Severe HHcy (~150 µM) was induced in cystathionine-β synthase heterozygous ($Cbs^{-/+}$) mice fed a high methionine diet. Vascular injury was introduced by carotid air-drying endothelium denudation. $CD34^+/VEGFR2^+$ cells were defined as putative EPCs. $CD34^+PCs$ from enhanced green fluorescent protein (EGFP) transgenic mice were adoptively transferred to mice after carotid injury. It was found that HHcy suppressed BM EPCs, inhibited post-injury EPC replenishment in the circulation, reduced $GFP^+$ PC homing to the injured vessel and re-endothelialization, and increased neointimal formation. CD34+PC transfusion partially reversed Hcy-suppressed re-endothelialization and proportionally rescued neointimal formation. In cultured primary EPCs-derived from human peripheral blood (hEPC), Hcy inhibited proliferation, adhesion, and migration in a dose dependent manner and suppressed integrin β1 expression and activity. A functional-activating β1 antibody rescued HHcy-suppressed adhesion and migration in hEPC. HHcy suppressed BM EPC generation, post-injury mobilization and homing, leading to impaired endothelial repair and worsen vascular remodeling.

The materials and methods used in these experiments are now described.

Methods and Materials

Gene-Targeted Mice and Hcy Measurement

Cbs mice were purchased from Jackson Laboratory (Bar Harbor, Me.) and backcrossed five generations for a total of twelve generations to achieve approximately 99.9% purity in a C57BL/B6 genetic background. Mice were genotyped by PCR as previously described (Watanabe, M et al., *Proceedings of the National Academy of Sciences of the United States of America*, 1995; 92:1585-1589). Animals were fed a standard rodent chow diet (0.43% methionine, TD 2018SX, Harlan Teklad, Madison, Wis.) before dietary intervention. Age-matched male Cbs littermates were selected for study at 8 weeks of age. Mice diet was switched to a custom designed low vitamin control diet (CT) (TD07793, Harlan Teklad, Madison, Wis.), or a high methionine (HM) diet (2% methionine, TD07794, Harlan Teklad, Madison, Wis.). After 8 weeks on the respective diets, mouse serum was collected for Hcy measurements using a Biochrom 30 amino acid analyzer (Cambridge, UK) as previously described (Cheng, Z et al., *Blood*, 2011; 118:1998-2006). Mouse protocols were approved by the Temple University Institutional Animal Care and Use Committee.

Peripheral Blood and Bone Marrow Cell Preparation

Peripheral blood (PB) was drawn for EPC population study via postorbital puncture with heparinized micro-hematocrit capillary tubes (BD, Franklin Lakes, N.J.). bone marrow cells were harvested from both tibias and femurs by inserting needles into the bone and washing with HBSS buffer (Cellgro, Mediatech Inc. Manassas, Va.) supplemented with 2% (v/v) FCS and filtered through 70 μM cell strainer (BD Falcon, San Jose, Calif.). Red blood cells in PB and BM were lysed with Ammonium-Chloride-Potassium Bicarbonate (ACK, 154.9 mM ammonium chloride, 10 mM Potassium Bicarbonate, 0.1 mM EDTA) for 5 min and 1 min at room temperature, respectively, followed with centrifugation for 7 min at 600×g and washed once with HBSS buffer. Cells were then suspended in HBSS supplemented with 2% (v/v) FCS and 0.09% (w/v) Sodium Azide (NaN3) for flow cytometry analysis.

Flow Cytometry Analysis of Mouse EPC

To investigate the effect of HHcy on the EPC population, circulating and BM-derived EPCs were analyzed by fluorescence-activated cell sorter (FACS) analysis. $CD34^+$/$VEGFR2^+$ cells were defined as putative EPCs. Isolated PB and BM cells were co-incubated with monoclonal antibodies against a stem cell marker CD34 (Alex-flour 647 conjugated anti-mouse CD34, clone HM34, Biolegend, San Diego, Calif.), and an endothelial lineage marker VEGFR-2 (phycoerythrin (PE)-conjugated anti-mouse VEGFR-2, clone 89B3A5, Biolegend, San Diego, Calif.). Flow cytometry analysis was performed on a FACS Calibur (BD Biosciences, San Jose, Calif.). Data were analyzed using the FlowJo software (Treestar, Inc., Ashland, Oreg.). Mononuclear cells (MNCs) are distinguished from granulocytes and lymphocytes based on their lower granular content as reflected in lower side-scatter light (SSC) and their larger cell size as reflected in higher forward scatter light (FSC) (FIG. 1B). $CD34^+$ and $VEGFR2^+$ double positive cells were identified from the MNCs population.

MACS Purification of Donor BM $CD34^+$PCs

EGFP mice were used as the donor strain. $GFP^+$ BM cells were harvested by flushing the femurs and tibias of adult animals (16-20 weeks age) as described above. $CD34^+$ PCs were obtained by magnetic cell separation (MACS) assay. Briefly, isolated BM cells were filtered through 30 μm nylon mesh (Miltenyi Biotec Inc. Auburn, Calif.) to remove cell clumps and counted. Firstly, BM cells are suspended in 400 μl of PBS buffer supplemented with 0.5% bovine serum albumin (BSA) and 2 mM EDTA, and incubated with purified monoclonal rat anti-mouse CD34 antibody (eBioscience, Inc. San Diego, Calif.) (100 μl to $10^8$ cells, for 15 minutes at 4° C.) and washed by adding 10 ml of PBS buffer and centrifuged at 300×g for 10 minutes. Secondly, to isolate $CD34^+$ cells, CD34 antibody-conjugated BM cells were suspended in 400 μl of PBS and incubated with 100 μl of goat anti-rat IgG microbeads (Miltenyi Biotec Inc. Auburn, Calif.) for 15 minutes at 4° C., washed by adding 10 ml of PBS buffer and centrifuged at 300×g for 10 minutes and suspended in 500 μL PBS. The cell suspension was loaded onto a MACS Column which is placed in the magnetic field of a MACS Separator. The magnetically-labeled $CD34^+$ PCs are retained within the column. The unlabeled cells run through the column. After removing the column from the magnetic field, the magnetically-labeled $CD34^+$ cells were immediately flushed out and collected by firmly pushing the plunger into the column after pipetting PBS buffer onto the column, counted and used for retro-orbital transfusion as described below.

Mouse Carotid Air-Dry Endothelium Denudation

Figures 2A, 2B, 2C, 2D, 2E, 2F, 2G:
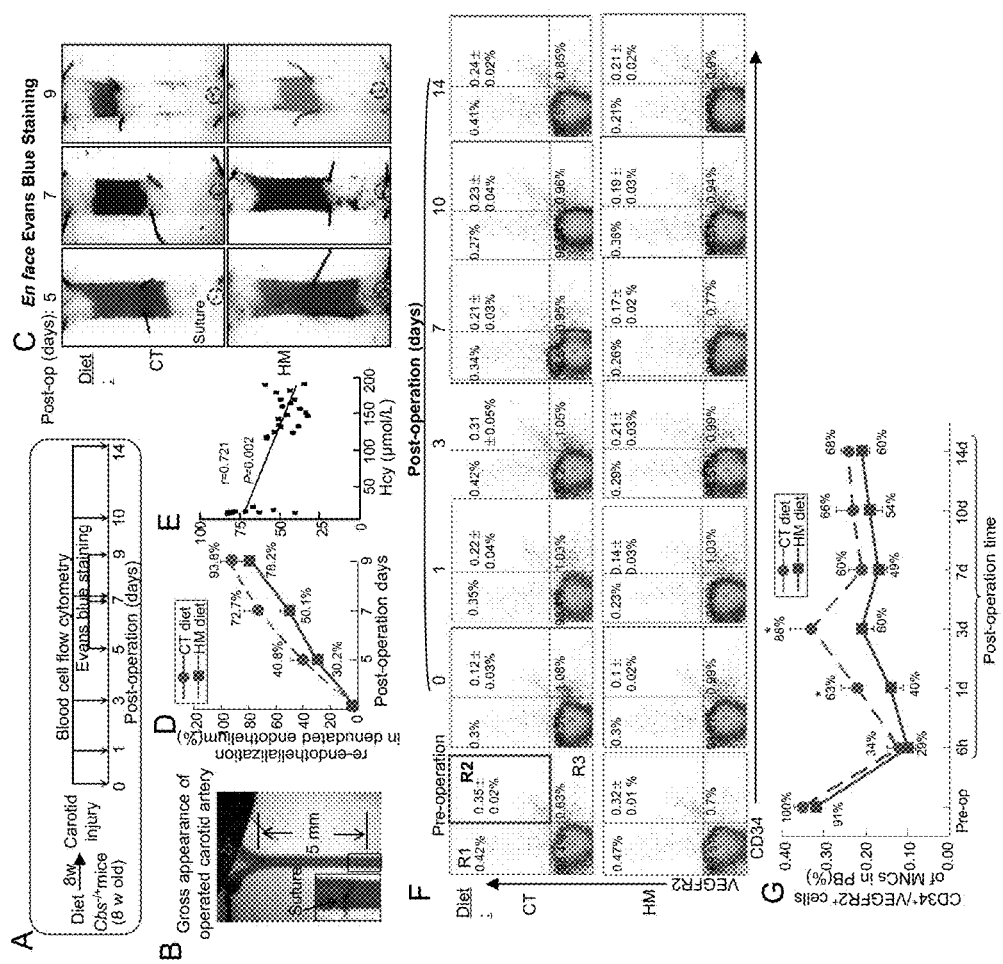
FIG. 2A through FIG. 2G, depicts the results of experiments demonstrating that HHcy impairs re-endothelialization and reduces $CD34^+/VEGFR2^+$ progenitor cell mobilization. $Cbs^{-/+}$ mice were fed a CT or HM diet at 8 weeks of age for an additional 8 weeks, and received carotid artery dilation and air-dry endothelial denudation surgery. Re-endothelialization was assessed by en face Evans blue staining on injured artery at the indicated times. Peripheral blood cells were collected, stained with antibodies against CD34 and VEGFR2, and analyzed by flow cytometry.

Carotid artery injury was induced as described previously (Tan, H et al., *Cardiovascular research*, 2006; 69:253-262). Briefly, after 8 weeks on their respective diets, mice were anesthetized with intraperitoneal sodium pentobarbital (50 mg/kg) and subjected to carotid artery dilation and air-dry endothelial denudation surgery. The left common carotids (LCC) of the mice were occluded and then dilated with 2 atmospheres of pressure for 1 min using an angioplasty inflation device. The inflation device was replaced with an air-filled 60 ml syringe controlled by a digital pump to deliver high-speed air for 15 min (30 ml/min) in order to dry and kill the endothelium. A suture was placed at the air-exit hole to mark the injury board (FIG. 2B). The injured carotid was then refilled with saline. The external carotid was ligated. Blood flow was restored. Four groups of mice were included in this study, CT and HM group with saline or $CD34^+$ transfusion, with at least 10 male mice each group. Animals were allowed to recover for 3 hours after surgery under close observation. Carotid arteries were harvested at indicated time points.

$CD34^+$ Cells Retro-Orbital Transfusion

Recipient and donor mice share all major histocompatibility antigens and are free of immunological barriers. $GFP^+CD34^+$ cells from EGFP transgenic mice were isolated by MACS assay as described above and transfused ($5\times10^6$ cells in 300 μl PBS) via retro-orbital injection into the recipient mice within 6 hours after carotid air-dry endothelium denudation surgery. To evaluate the homing of $CD34^+$ to the injured artery area, denuded carotid arteries were examined by en face and cross-section immunochemistry staining using an antibody against GFP.

$CD34^+$ PC In Vivo Imaging

To trace transfused cells in mice, BM-derived $CD34^+$ cells were stained with IRDye800CW NHS ester (Li-Cor Biosciences, Lincoln, Nebr.), a near infrared fluorophore with excitation/emission of 778 nm/794 nm, where low absorption coefficients of tissues allow greater optical sensitivity, deeper tissue penetration, and low auto-fluorescence, and can be used as an optical imaging tool for tracing labeled cells in mice. IRDye800CW NHS was prepared in a stock concentration of 1 mg/ml in dimethylsulphoxide (DMSO). BM-derived $CD34^+$ cells from donor mice were stained with IRDye800CW NHS (50 m/ml per $1\times10^7$ cells) and incubated for 2 h at 4° C. Cells were washed three times with PBS and re-suspended in PBS for injection. Labeled $CD34^+$ cells were transfused into recipient mice via retro-orbital injection immediately after carotid artery injury. The distribution of the transfused cells was traced by tracking IRDye Infrared dyes imaging over the first 30 min, 90 min, 24 h, 48 h, and 72 h post-transfusion.

En Face Staining of Injured Artery

En face staining was performed on whole-mounted vessels to visualize the damaged endothelium, examine re-endothelialization, and quantify transfused $GFP^+$ cell area in an injured vessel. For re-endothelialization analysis, mice were sacrificed 7 days after carotid injury. Anesthetized mice were perfused with 5% Evans blue, washed with PBS, and fixed with 10% neutral buffered formalin. Both the LCC and right common carotid (RCC) were dissected, cut longitudinally, pinned on a silicon dissecting dish, and photographed under a dissecting microscope (FOSTEC, Stemi 2000-C, Barrington, N.J.). De-endothelialized areas were defined as those areas that stained blue between the branch point of the external carotid at the proximal end and the suture placed at the air-exit hole at the distal end, using the updated Image J (National Institutes of Health (NIH), Bethesda, Md.). The re-endothelialization rate was calculated by dividing the de-endothelialization area by the remaining blue stained area and subtracting that figure from 100%. Anti-GFP antibody (Invitrogen, molecular probes, Inc, Eugene, Oreg.) immunostaining was performed to identify homed $GFP^+$ cells. $GFP^+$ cell numbers were counted in 5 different areas under a dissecting microscope with 0.6× objective magnifications in the en face carotid arteries. Cell nuclei were stained with 4',6-diamidino-2-phenylindole (DAPI) and counted for average number per surface area (in square millimeters).

Immunochemistry Analysis on Cross-Section of Injured Carotid Artery

Mice were perfused with PBS 14 or 28 days post-injury. The injured LCC segment was excised from the suture line at the air-exit hole to the carotid bifurcation, embedded in OCT compound (Tissue Tek; Sakura Finetek USA, Torrance, Calif.), and quick-frozen on dry ice and stored at −80° C. Serial cross/longitude sections (10 μm) of the injured carotid arteries were sectioned on a Leica cryostat as previously described (Tan, H et al., Cardiovascular research, 2006; 69:253-262) and mounted on Super-frost Excell microscope slides (Fisher Scientific, Pittsburgh, Pa.). Cryosections were post-fixed in Acetone for 10 minutes prior to immunochemistry staining. For CD31 and GFP co-staining, slides were pre-incubated with 5% normal goat serum for 30 minutes, incubated with a rabbit anti-GFP polyclonal antibody (1:200, Invitrogen, molecular probes, Inc, Eugene, Oreg.) overnight, a rat anti-mouse CD31 monoclonal antibody (1:150, BD Pharmingen™, San Diego, Calif.) overnight again, a donkey anti-mouse IgG-rhodamine red-X (RdX) antibody (1:500, Jackson Immunoresearch Laboratories, West Grove, Pa.), and finally with DAPI (100 ng/ml) for nuclear staining. Slides were washed for 3 times with PBST after each antibody incubation, each time 10 min, and finally mounted with fluorescent mounting medium for fluorescent microscopic analysis. Vessel cross-sections from 28 days post-injury were stained with an Elastic stain kit (Sigma-Aldrich Corporation, St. Louis, Mo.) according to manufacturer instructions. All sections were examined under a microscope (Axioskop 2 Plus, Carl Zeiss, Thornwood, N.Y.) for morphometric analyses. External elastic lamina, internal elastic lamina, and lumen circumference as well as medial and neointimal area were measured using "Image J" software as described in method section (En face staining of injured artery). The neointimal area was defined as the region between the lumen and internal elastic lamina. The medial wall (MW) was defined as the region between the internal and external elastic laminas. NI and MW areas were measured using the Image J program. The percentage of lumen narrowing was calculated as 100×(area of the NI÷area inside the internal elastic lamina).

Human EPC Isolation, Culture and Characterization

In this study EPCs refer to endothelial colony-forming cells (ECFCs) and their progenitor cell capacities were characterized as described (Wu, Y et al., J Thromb Haemost, 2010; 8:185-193; Wang, H et al., Circulation research, 2004; 94:843 and Stellos, K et al., Eur Heart J., 2009; 30:584-593). Briefly, human blood was collected from healthy volunteer donors. All volunteers had no risk factors of CVD including hypertension, diabetes, smoking, positive family history of premature CVD and hypercholesterolemia, and were all free of wounds, ulcers, retinopathy, recent surgery, inflammatory, malignant diseases, and medications that may influence EPC kinetics. After dilution with HBSS (1:1), blood was overlaid onto Histopaque 1077 (Sigma-Aldrich Co. LLC, St. Louis, Mo.) in the ratio of 1:1 and centrifuged at 740 g for 30 minutes at room temperature. Buffy coat MNCs were collected and centrifuged at 700 g for 10 minutes at room temperature. MNCs were cultured in collagen type I (BD Bioscience, San Diego) (50 m/ml)-coated dishes with EBM2 basal medium (Lonza Inc., Allendale, N.J.) plus standard EGM-2 SingleQuotes (Lonza Inc., Allendale, N.J.) that includes 2% fetal bovine serum (FBS), EGF (20 ng/ml), hydrocortisone (1 μg/ml), bovine brain extract (12 μg/ml), gentamycin (50 μg/ml), amphotericin B (50 ng/ml), and epidermal growth factor (10 ng/ml). Colonies appeared between 5 and 22 days of culture were identified as a well-circumscribed monolayer of cobblestone-appearing cells. ECFCs with endothelial lineage markers expression, robust proliferative potential, colony-forming, and vessel-forming activity in vitro are defined as EPCs as described (Wang, H et al., Circulation research, 2004; 94:843 and Stellos, K et al., Eur Heart J., 2009; 30:584-593). Passage 4 to 6 EPCs were used for experiments. For a brief characterization, endothelial phagocytosis function was confirmed by incubating EPC in 4-well chamber slide with 1, 1-dioctadecyl-3, 3, 3, 3-tetramethylindocarbocyanine (DiI)-labeled acetylated low-density lipoprotein (acLDL) (Biomedical Technologies, Inc., Stoughton, Mass.) (5 m/ml) at 37° C. for 1 h, washed 3 times for 15 min in PBS, and then fixed with 2% paraformaldehyde for 10 min. Cells were then incubated with FITC conjugated UEA-1 (Ulex europaeus agglutinin) (10 m/ml) (Sigma-Aldrich Corporation, St. Louis, Mo.) for 1 h at room temperature, which is capable of binding with glycoproteins on the cell membrane to allow visualization of the entire cell. Cell integrity was examined by nuclear staining with DAPI (100 ng/ml). After staining, cells were imaged with high-power fields under an inverted fluorescent microscope (Axiovert 200, Carl Zeiss, Thornwood, N.Y.) at 200× magnification and quantified using Image J software.

EPC Function: Adhesion, Migration, and Proliferation Assays

EPC, at passage 4 to 6, were treated with L-Hcy and examined for Adhesion, Migration, and Proliferation function. L-HCy was freshly prepared by reducing L-homocystine with a 2-fold molar excess of dithiothreitol for 30 minutes at 37° C., pH 8.0, as described (Jamaluddin, M D et al., Blood, 2007; 110:3648-3655). All chemicals, if not specified above, were purchased from Sigma-Aldrich.

Adhesion Assay:

EPC adhesion to extracellular matrix (ECM) was evaluated as previously described. Briefly, confluent EPCs were first incubated with L-Hcy (50 to 250 μmol/L) for 48 hours. For the integrin mediated adhesion assay, confluent EPCs were incubated with L-Hcy for 48 h in the absence or presence of a function-activating antibody 12G10 against β1 integrin (Millipore, Billerica, Mass.) or isotype IgG1 controls (Millipore, Billerica, Mass.), respectively. After corresponding treatment, EPCs ($1\times10^5$) were seeded on fibronectin (100 μg/ml) coated-24 well plates in EGM2 medium and incubated for 1 hour at 37° C. Adherent cells were photographed with high-power fields under an inverted fluorescent microscope (Axiovert 200, Carl Zeiss, Thornwood, N.Y.) at 200× magnification and quantified by counting the attached cells using image J.

Scratch Wound Assay:

EPC migration was evaluated using a scratch wound assay as previously described (Tan, H et al., Cardiovascular research, 2006; 69:253-262). Confluent EPCs cultured on 35 mm dishes were firstly incubated with L-Hcy (50 to 250 μmol/L) for 24 hours. For integrin mediated migration, confluent EPCs were incubated with L-Hcy for 24 h in the absence or presence of function-activating antibody 12G10 against β1 integrin (Millipore, Billerica, Mass.) or isotype IgG1 controls (Millipore, Billerica, Mass.), respectively. Cells were then wounded by scratching with an 1 ml micropipette tip, rinsed with PBS, and then incubated with consistent treatment for 20 h. EPC migration was photographed under an inverted fluorescent microscope (Axiovert 200, Carl Zeiss, Thornwood, N.Y.) at 100× magnification, measured using Image J, and expressed as the percentage of distance migrated divided by the length of the initial wound.

Proliferation Assay:

$^3$H thymidine incorporation assay was used to detect EPC proliferation activity as previously described (Tan, H et al., Cardiovascular research, 2006; 69:253-262). $^3$EPCs were seeded onto 24-well plates (5×10$^4$ cells/well) in EGM2 medium and exposed to L-Hcy (50 to 250 μmol/L) for 24 h after grown to 70-80% confluence. EPCs were labeled with 1 μCi/ml [methyl-$^3$H] thymidine (DuPont/NEN, Boston Mass.) for the last 4 h. Incorporated [methyl-$^3$H] thymidine was measured in a liquid scintillation counter (PerkinElmer Inc. Waltham, Mass., USA).

Detection of Integrin Expression and Activity

EPCs were incubated with L-Hcy (250 μmol/L) in EGM2 medium for 48 hours, harvested with trypsin, and re-suspended in PBS supplemented with 2% fetal calf serum (FCS) and 2 mmol/L EDTA. To examine β1 integrin expression, EPCs were incubated with monoclonal antibody against β1 integrin (PE-Cy™5 conjugated mouse anti-human CD29, clone MAR4, BD Pharmingen™, San Diego, Calif.) or isotype control (PE-Cy™5 conjugated Mouse IgG1, κ, BD Pharmingen™, San Diego, Calif.) for 30 minutes at 4° C. For αvβ3 integrin expression, cells were incubated with monoclonal antibody against αvβ3 integrin (PE conjugated mouse anti-human CD51/CD61, clone 23C6, BD Pharmingen™, San Diego, Calif.) or isotype control (PE conjugated Mouse IgG1, κ, BD Pharmingen™, San Diego, Calif.). To examine integrin activity, EPCs were incubated with monoclonal antibody against β1 integrin activation epitope HUTS-21 (PE conjugated mouse anti human HUTS-21, clone HUTS-21, BD Pharmingen™, San Diego, Calif.) or isotype control (PE conjugated IgG2a, κ, BD Pharmingen™, San Diego, Calif.) for 15 minutes at 37° C. Integrin expression and activity were measured using flow cytometry analysis and quantified using the FlowJo software (Treestar, Inc., Ashland, Oreg.).

Statistical Analysis

Statistical analyses were performed with Sigma-Stat 2.03 (SPSS Science, Chicago, Ill.). Results are expressed as the mean±SEM. Statistical comparison of single parameters between two groups was performed using the independent t test. Kruskal-Wallis One-way ANOVA with Dunnett's test was used to compare the means of multiple groups. Correlations between plasma Hcy concentration and the variables were performed using Spearman correlation analysis. All in vitro assays were repeated 3 times. A probability value of $p<0.05$ was considered to be significant.

The results of the experiments in this experimental example are now described.

HHcy Reduces the CD34$^+$/VEGFR2$^+$ Cells in the BM of HHcy Mice

Severe HHcy was induced by 8 weeks of HM diet in the Cbs$^{-/+}$ mice. Serum Hcy levels were increased from 5.8±0.56 μmol/L to 152.6±12.4 μmol/L (p=0.003). Hcy levels were not largely changed in these two groups of mice when BM CD34$^+$PCs were transfused (becoming 7±0.81 μM and 171.3±13.6 μM) (FIG. 1A). HM diet has no effect on body weight and organ weight (heart, lung, liver, kidney and spleen) relative to tibia length in the presence and absence of exogenous CD34$^+$PCs transfusion (FIG. 7A-FIG. 7F).

CD34$^+$/VEGFR2$^+$ cells, a population having EPC potential (FIG. 1B), were assessed as surface markers CD34$^+$ and VEGFR2$^+$ have been commonly used for EPC identification (Breen, D M et al., Arteriosclerosis, thrombosis, and vascular biology, 2009; 29:1060-1066). Severe HHcy reduced BM CD34$^+$/VEGFR2$^+$ cells (0.52±0.06% of MNC population) compared with controls (0.71±0.08%, p=0.04). Whereas, circulating CD34$^+$/VEGFR2$^+$ cells were not changed in HHcy mice compared with controls (0.29±0.05% vs 0.32±0.04%) (FIG. 1C-FIG. 1D). Serum Hcy levels are negatively correlated with CD34$^+$/VEGFR2$^+$ cell population in BM in HHcy mice (FIG. 1E).

HHcy Impairs Re-Endothelialization and Reduces CD34$^+$/VEGFR2$^+$ Cell Mobilization As described in FIG. 2A, re-endothelialization and CD34$^+$/VEGFR2$^+$ cell mobilization was examined in Cbs mice following an air-dried carotid artery injury (Tan, H et al., Cardiovascular research, 2006; 69:253-262). Endothelial repair was monitored in the injured vessel segment, approximately 5 mm from the bifurcation point of external carotid artery and internal carotid artery to the air-exit hole, which is marked by placing a suture (FIG. 2B). Severe HHcy delayed re-endothelialization characterized by en face Evans blue staining (FIG. 2C). At day 5 post carotid artery injury, re-endothelialization was reduced to 30.2±7.6% in severe HHcy mice vs 40.8±8.7% in CT mice (p>0.05); at day 7, 50.1±6.6% vs 72.7±10.2% (p=0.025); and day 9, 78.2±10.8% vs 93.8±6.7%, (p=0.032) (FIG. 2D). Serum Hcy levels are negatively correlated with re-endothelialization in Cbs mice (FIG. 2E). To examine post-injury CD34$^+$/VEGFR2$^+$ cell mobilization, the circulating CD34$^+$/VEGFR2$^+$ cell population was examined at indicated times (pre-injury, 6 hours, 1, 3, 7, 10, and 14 days post-injury). It was found that, 6 hours after the air-dry carotid artery procedure, the circulating CD34$^+$/VEGFR2$^+$ cell population sharply dropped from 0.32±0.01% and 0.35±0.02% to 0.1±0.02% and 0.12±0.03% in HHcy and CT mice, respectively. Three days after carotid injury, the circulating CD34$^+$/VEGFR2$^+$ cell population was almost recovered to the basal level in the control mice (0.31±0.05%), but severely impaired in HHcy mice (0.21±0.03%, p=0.029), 60% of the basal level, a 40% reduction. The CD34$^+$/VEGFR2$^+$ cell population was maintained at a steady state level during days 7 to 14 in both HHcy and control mice (0.21±0.02% vs 0.24±0.02%, p>0.05) (FIG. 2F-FIG. 2G). These data demonstrate an acute recruitment of CD34$^+$/VEGFR2$^+$ cells for post-injury vascular repair and a reduced mobilization of CD34$^+$/VEGFR2$^+$ cells from the BM to replenish the circulating population in HHcy mice.

HHcy Inhibits Mobilization of Endogenous CD34$^+$/VEGFR2$^+$ Cells

Figures 3A, 3B, 3C, 3D:
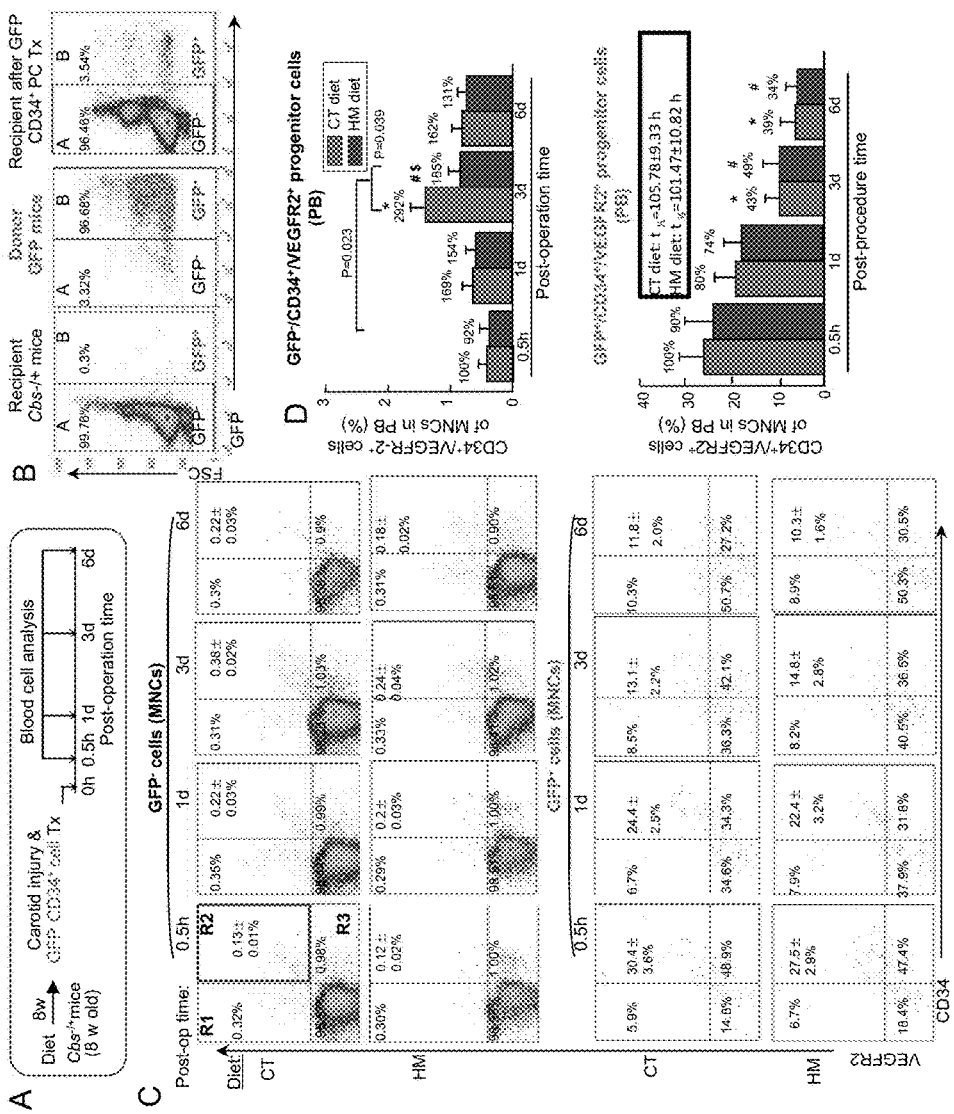
FIG. 3A through FIG. 3D, depicts the results of experiments demonstrating that HHcy inhibits mobilization of endogenous $CD34^+/VEGFR2^+$ progenitor cells. $Cbs^{-/+}$ mice were fed a CT or HM diet at 8 weeks of age for an additional 8 weeks. BM $CD34^+$ cells from EGFP transgenic mice were transfused into $Cbs^{-/+}$ mice with a CT or HM diet after air-dry carotid artery injury. Mouse peripheral blood cells were collected, stained with antibodies against CD34 and VEGFR2, and analyzed by flow cytometry.

To validate the inhibitory effect of HHcy on CD34$^+$/VEGFR2$^+$ cell mobilization, an adaptive cell transfer procedure was employed by transfusing donor GFP$^+$ BM CD34$^+$ PCs into Cbs mice immediately after artery injury (FIG. 3A). The recipient mice have about 3.54% of GFP$^+$ cells in the circulation (FIG. 3B). It was found that circulating GFP$^+$CD34$^+$/VEGFR2$^+$ cells, the exogenous cells from donor mice, were gradually reduced at indicated time points (0.5 hour, 1, 3, and 6 days post-injury) in a similar fashion in both HHcy and control mice. The transfused GFP$^+$CD34$^+$/VEGFR2$^+$ cells were reduced to 43% and 49% at day 3 and to 39% and 34% at day 6 post-carotid injury and have a half-life ($t_{1/2}$) of 105.78±9.33 hr and 101.47±10.82 hr in control and HHcy mice (p=0.62, FIG. 3C-FIG. 3D). The circulating GFP$^-$CD34$^+$/VEGFR2$^+$ cells, the endogenous cells of the recipient mice, were gradually recovered and reached the peak at day 3 after the procedures in the control mice (0.38±0.02), but remained at the lower levels of 0.24±0.04% (p=0.001) in HHcy mice. This is consistent with data presented in FIG. 2 and further demonstrated that HHcy inhibits post-injury BM CD34$^+$/VEGFR2$^+$ cells replenishment in the circulation.

Figures 4A, 4B, 4C, 4D, 4E, 4F:
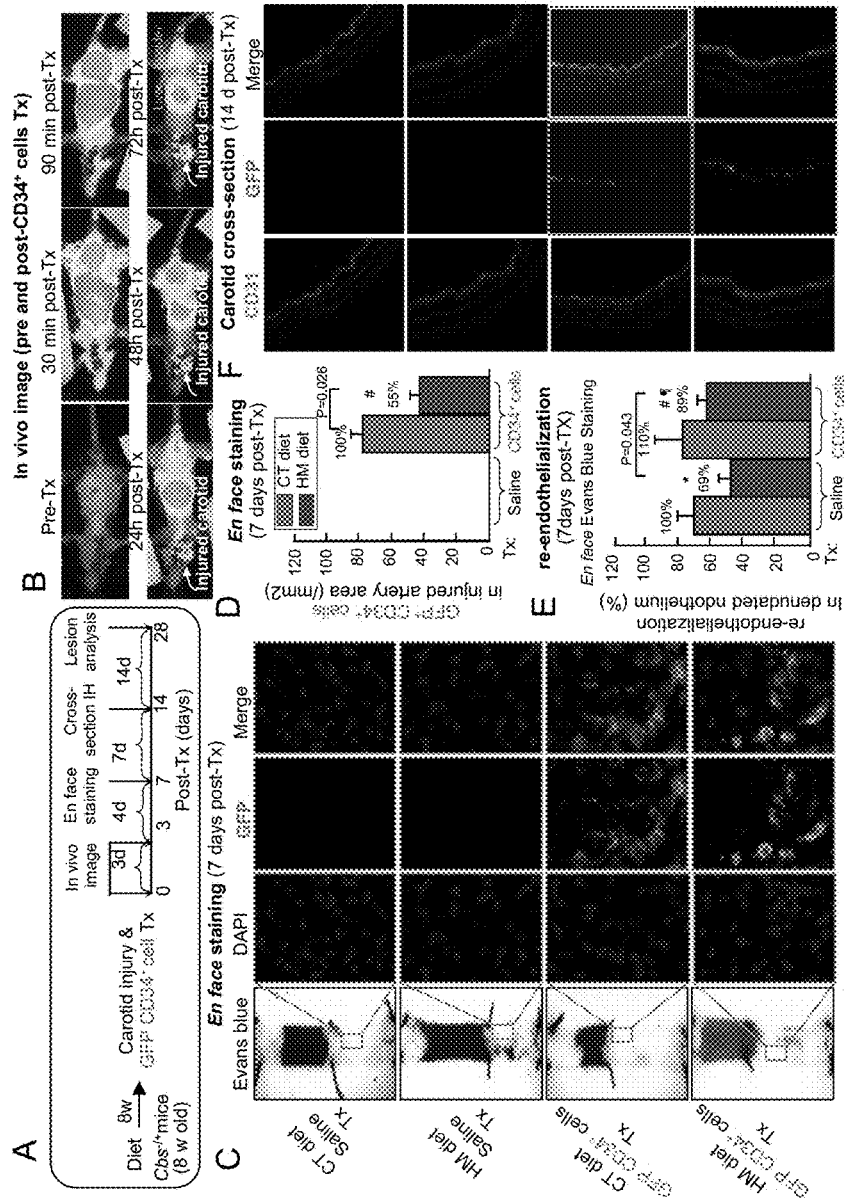
FIG. 4A through FIG. 4H, depicts the results of experiments demonstrating that HHcy inhibits $CD34^+$ cells homing to denudated endothelium. $CD34^+$ cells transfusion improves HHcy-suppressed post-injury re-endothelialization and reduces vascular remodeling. $Cbs^{-/+}$ mice were fed a CT or HM diet at 8 weeks of age for an additional 8 weeks. BM $CD34^+$ cells were isolated from EGFP transgenic mice and immediately transfused into $Cbs^{-/+}$ mice with CT or HM diet after air-dry carotid artery injury.

HHcy Inhibits CD34$^+$PC Homing to Denuded Endothelium and CD34$^+$PC Transfusion Improves Re-Endothelialization in HHcy Mice To track the distribution of CD34$^+$PCs following transfusion, donor BM CD34$^+$PCs were labeled with IRDye800CW, a near far-red dye, and the transfused CD34$^+$ PCs were traced in the mice over the 30 min, 90 min, 24 h, 48 h, and 72 h post CD34$^+$PC transfusion and carotid injury by in vivo imaging. As shown in FIG. 4B, IRDye800CW-labeled donor BM CD34$^+$PCs were found mostly in the liver and bladder area 30 and 90 min following transfusion, residing in the area of injured carotid artery (red dotted circle) at 24 h after carotid artery injury and remained in this area at 72 h. To further evaluate the homing and contribution of donor BM-derived PCs to post-injury re-endothelialization, GFP$^+$ PCs were examined in the injured carotid specimens 7 and 14 days after artery injury by GFP En face staining and longitude section analyses. Islets of transplanted GFP$^+$ cells within the re-endothelialized area were detected and had a 45% decrease in the number of GFP$^+$ cells/mm$^2$ in HHcy mice as compared with controls (FIG. 4C-FIG. 4D). GFP$^+$ cells were strictly restricted to the injury site and not detectable in uninjured vessels, or in the vessels in which mice did not receive GFP$^+$ cell transfusion. Moreover, Evans blue staining showed that post-injury re-endothelialization with CD34$^+$ PCs transfusion was slightly improved by 110% in the control mice, and largely improved HHcy-suppressed re-endothelialization from 69% to 89% (p=0.043) in HHcy mice (FIG. 4E). To confirm the contribution of transfused GFP$^+$CD34$^+$ PCs in re-endothelialization, immunohistochemical analysis showed that GFP$^+$CD31$^+$ cells were detected lining on the intraluminal margin of the neointimal area 14 days after vessel injury (FIG. 4F). The endothelium was intact and completely repaired at day 14 after vessel injury in both groups.

BM-Derived CD34$^+$ PCs Transfusion Reduces Neointimal Formation in HHcy Mice

Figures 4G, 4H:
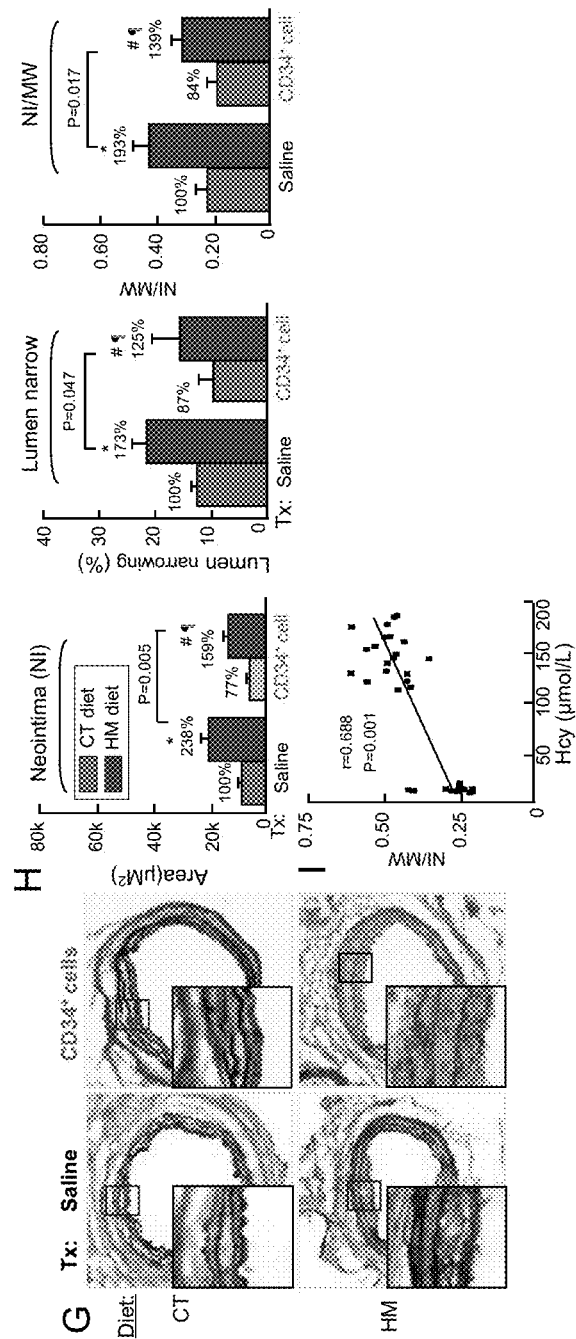

To investigate whether CD34$^+$ PCs transfusion reduce post-injury vascular remodeling, vascular lesions were characterized 28 days after carotid artery injury (FIG. 4A, FIG. 4G). As shown in FIG. 4G, HHcy increased post-injury neointimal formation in HHcy mice, 238% (19999±2791 μm$^2$) vs 100% (8388±1222 μm$^2$) (FIG. 4H). CD34$^+$PC transfusion reduced neointimal area from 100% to 77%, a 23% reduction, in the control mice, and from 238% to 159%, a 33% reduction, in HHcy mice. Similarly, CD34$^+$PC transfusion reduced lumen narrowing from 172% to 125% in HHcy mice (21.3±2.6% vs 15.4±4.9%, p=0.047) (FIG. 4H). Vascular remodeling, measured by the ratio of neointima to media wall area (NI/MW ratio), was significantly increased by 193% in HHcy mice as compared with control mice (0.22±0.04 vs 0.42±0.06, p=0.001) (FIG. 4H). CD34$^+$PCs transfusion significantly decreased NI/MW ratio by 28% in HHcy mice, 193% (0.42±0.06) vs 139% (0.30±0.04) (p=0.017). A beneficial trend of CD34$^+$PC transfusion was observed in control mice where CD34$^+$PC therapy reduced NI area, lumen narrowing and NI/MW ratio (FIG. 4H). Furthermore, neointimal hyperplasia positively correlated with plasma Hcy levels in Cbs mice (FIG. 4I).

Hcy Inhibits Adhesion, Migration, and Proliferation of hEPCs

Figures 5A, 5B, 5C, 5D, 5E, 5F, 5G:
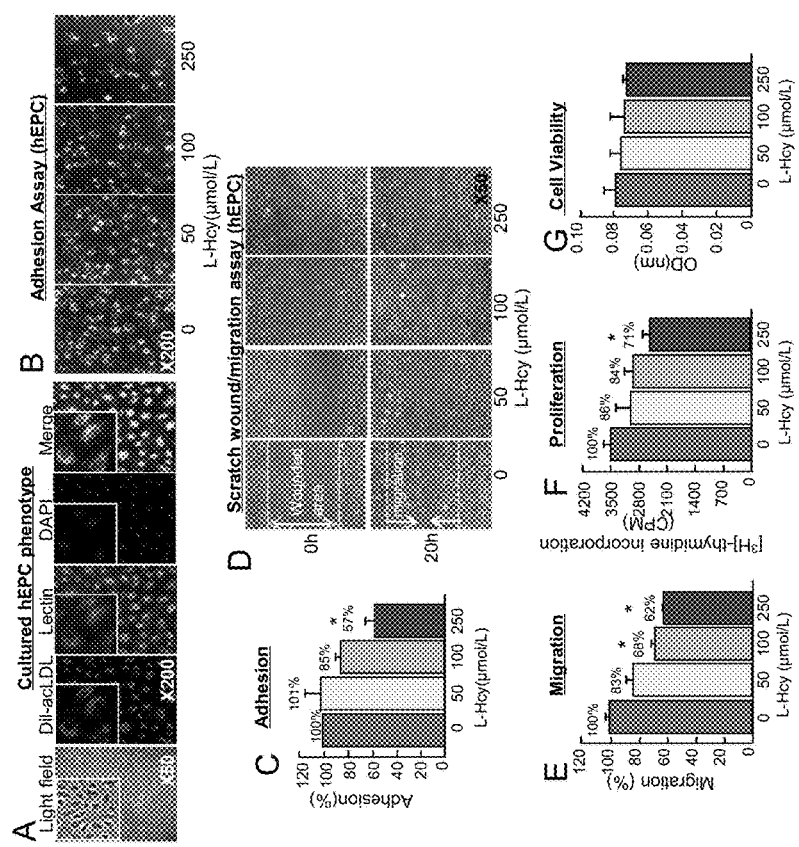
FIG. 5A through FIG. 5G, depicts the results of experiments demonstrating that Hcy inhabits adhesion, migration, and proliferation of hEPC. hEPCs were isolated and cultivated from the peripheral blood of a healthy donor. Confluent hEPCs were treated with L-Hcy at indicated concentrations for functional studies as described in the section of Methods.

To further examine the effects of Hcy on the EPC biological phenotype, a cultured primary human EPC model from PB was established using a colony forming assay. Putative EPCs express PC and endothelial lineage markers, exhibit robust proliferative potential, and colony-forming and vessel-forming activity (Kokubo, T et al., *Journal of vascular surgery*, 2007; 45 Suppl A:A33-38). hEPCs have typical cobblestone endothelial morphology and are positive for Dil-labeled acLDL uptake and lectin binding, which are markers for endothelial phagocytosis function and cell membrane glycoprotein, respectively (FIG. 5A). Cell adhesion to fibronectin-coated dishes, a major feature for EPC homing to the injured vasculature, is impaired in response to Hcy treatment in a dose response manner. L-Hcy (250 μmol/L) reduced EPC adhesion to fibronectin to 57% compared with the control (0.13±0.006 vs (0.06±0.008 (OD630 nm, p=0.001)) (FIG. 5B-FIG. 5C). Hcy (100 μmol/L and 250 μmol/L) significantly reduced hEPC migration to 68% (54.6±2.8, p=0.03) and 62% (49.7±1.1 p=0.018) (FIG. 5D-FIG. 5E). The effect of L-Hcy on EPC proliferation and viability was further examined by [$^3$H] thymidine uptake and crystal violet staining. HHcy dose sensitively inhibited DNA synthesis but has no effect on EPC viability (FIG. 5F-FIG. 5G).

Hcy Inhibits β1 Integrin Expression/Activity in hEPCs

Figures 6A, 6B, 6C, 6D, 6E, 6F, 6G, 6H:
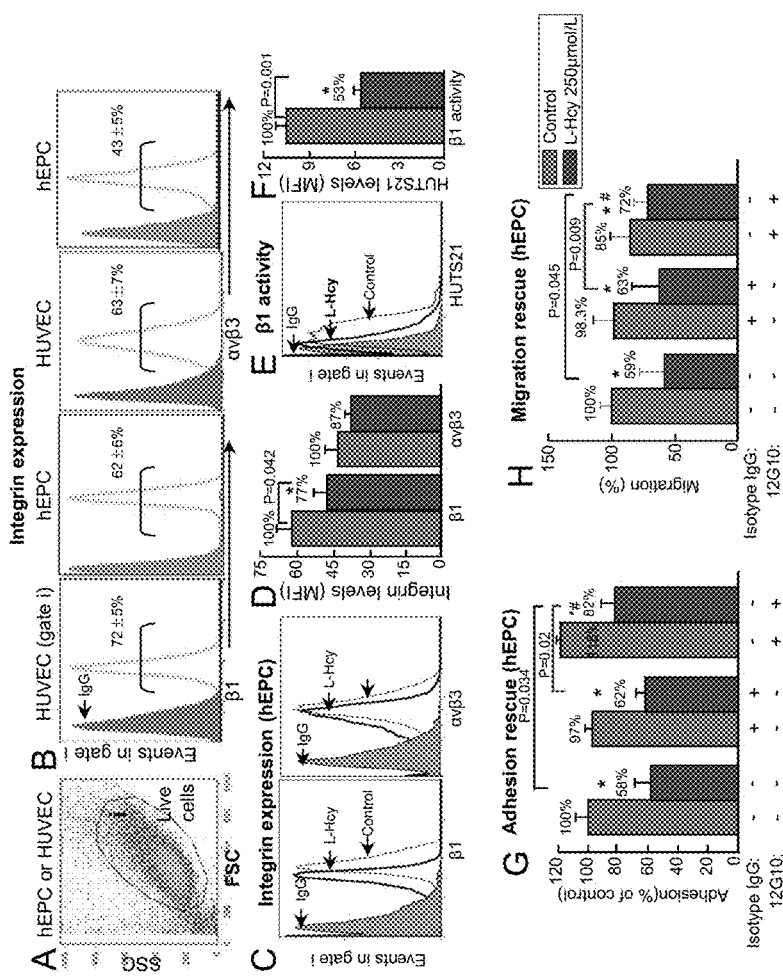
FIG. 6A through FIG. 6H, depicts the results of experiments demonstrating that Hcy inhibits β1 integrin expression/activity in hEPCs. hEPCs were isolated and cultivated from the peripheral blood of a healthy donor. Confluent hEPCs treated with L-Hcy (250 µmol/L) for 48 hours were examined for integrin expression and activity by flow cytometry. Cells were harvested with trypsin and incubated with PE-Cy5-conjugated CD29 antibody (for β1), PE-conjugated CD51/CD61 antibody (for αvβ3), and activation-dependent epitope HUTS21 of β1 integrin as an indicator of β1 integrin activity. Isotype control PE-Cy5-labeled, PE labeled antibodies were used as an IgG control.
Figures 7A, 7B, 7C, 7D, 7E, 7F:
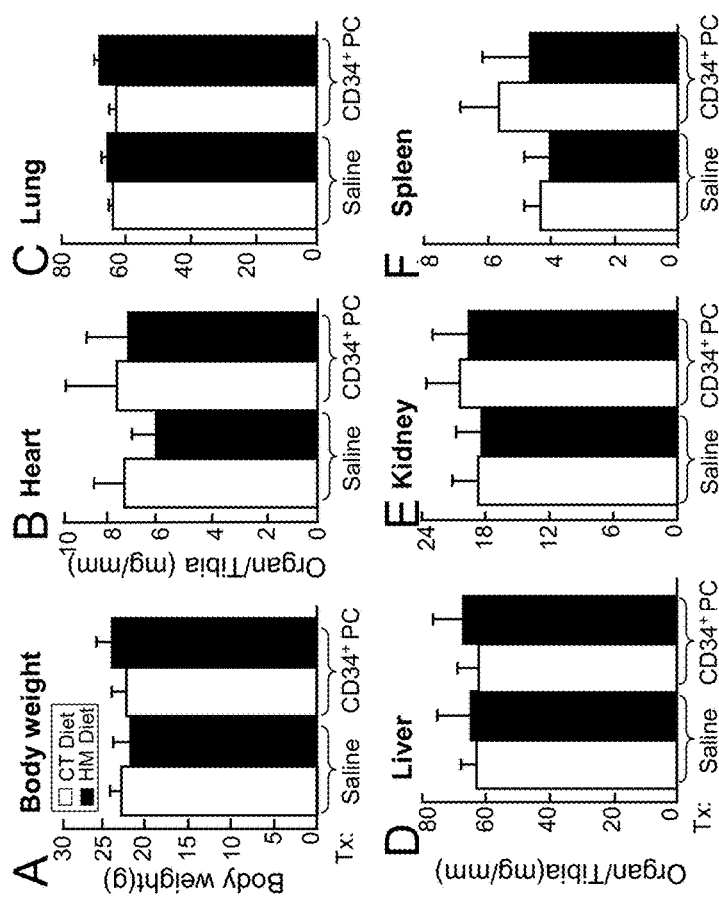
FIG. 7A through FIG. 7F, depicts the results of experiments demonstrating that HHcy reduces the CD34+/VEGFR2+ cells in the BM. CBS$^{-/+}$ mice were fed a CT or HM diet at 8 weeks of age for additional 8 weeks. BM CD34+ cells were isolated from EGFP transgenic mice and immediately transfused via retro-orbital injection into CBS$^{-/+}$ mice with CT or HM diet after air-dry carotid artery injury as described in FIG. 3A. Mouse body weight, heart, lung, liver, kidney, spleen and tibia were measured 28 days after carotid artery injury.

EPCs adhere to ECM proteins or cells via specific integrin receptors. To assess the effect of Hcy on integrin expression in EPCs, β1 and αvβ3 integrins were examined, both of which mediate adhesive interactions between cells and ECM adhesion after vessel injury (Walter, D H et al., *Circulation*, 2002; 105:3017-3024 and Kokubo, T et al., *Journal of vascular surgery*, 2007; 45 Suppl A:A33-38). β1 integrin is abundantly expressed in hEPCs and HUVECs (62±6% and 72±5%). αvβ3-integrin is expressed at relatively lower levels (43±5% and 63±7%) in hEPCs and HUVECs (FIG. 6B). L-Hcy (250 μmol/L) reduced β1 integrin to 77% (FIG. 6C-FIG. 6D) compared to the control cells. Hcy dramatically inhibited β1 integrin activity to 53% as determined by activation-dependent epitope HUTS21 antibody of β1 integrin by flow cytometry analysis (FIG. 6E-FIG. 6F). Co-incubation with a β1 integrin antibody, 12G10, which recognizes the fibronectin-induced binding site and increases β1 integrin binding to fibronectin, significantly rescued Hcy-suppressed adhesion from 62% to 82% in hEPC (FIG. 6G). Similarly, 12G10 antibody co-incubation in the presence of L-Hcy (250 μmol/L) rescued Hcy-suppressed hEPC migration (FIG. 6H). These data demonstrated that Hcy suppresses EPC adhesion and migration, at least, partially via β1 integrin inhibition.

Hyperhomocysteinemia Inhibits CD34$^+$/VEGFR2$^+$ Progenitor Cell Mobilization and Homing in Post-Injury Vascular Repair in Mice and Suppresses β1 Integrin in Human Endothelial Progenitor Cells The vascular endothelium is the monolayer lining the lumen of the vasculature and separates the vascular wall from the circulation. The loss of endothelial integrity is an inciting event, which triggers the onset of vascular smooth muscle cell (SMC) proliferation and migration that contribute to the establishment of vascular remodeling. Endothelial regeneration is a local process involving EC proliferation and migration from intact ECs adjacent to the injured area (Carmeliet, P et al., *The American journal of pathology*, 1997; 150:761-776). It is agreeable that circulating and BM-derived EPCs are able to home to the injured endothelium, and facilitate re-endothelialization. EPC therapy has been considered as a new strategy in regenerative medicine for vascular repair. However, EPC biology and regulatory mechanisms in healthy and disease situations are largely unknown.

The present study underscores the importance of BM-derived PC mobilization, homing to the site of vascular injury, and facilitating re-endothelialization and preventing neointimal formation. Demonstrated here are the following novel findings: (1) severe HHcy suppresses CD34$^+$/VEGFR2$^+$ PC generation in the BM and inhibits its post-injury mobilization, which are associated with delayed re-endothelialization and increased vascular remodeling in Cbs deficient mice; (2) HHcy reduces PC homing and contribution to endothelial regeneration; (3) transfusion of BM-derived CD34$^+$ PCs improves re-endothelialization and reduces neointimal formation in Cbs deficient mice; (4) Hcy inhibits human EPC migration and adhesion via β1 integrin reduction/inactivation.

EPCs are determined to be differentiated into ECs and can contribute to endothelial repair. Circulating EPCs are mainly derived from BM and can be characterized by both stem cell surface markers (CD34, Sca1, or c-kit) and EC surface markers (VEGFR2, CD31, VWF, or E-cadherin). Previously, different combinations of surface markers have been used to define mouse EPCs, such as CD34/VEGFR2, Sca1-1/VEGFR2, c-kit/CD31, c-kit/Tie-2, and VEGFR2/E-cadherin (Heeschen, C et al., *Blood*, 2003; 102:1340-1346; Iwakura, A et al., *Circulation*, 2003; 108:3115-3121; Patschan, D et al., *American journal of physiology. Renal physiology*, 2006; 291:F176-185; and Nakajima, M et al., *Cell Biol Int.*, 2006; 30:239-243). In this study, CD34/VEGFR2 was used as the characteristics of mouse EPCs, as CD34 is a hematopoietic stem cell and progenitor cell marker, and VEGFR2 is a well-recognized endothelial cell marker.

It was found that circulating EPC levels sharply dropped to 34% 6 hours after surgery, demonstrating the acute recruitment of circulating EPCs to the injured tissue. Three days after the surgery, the circulating EPC population is replenished to 88% as a result of acute active post-injury EPC regeneration and mobilization from the BM in the control mice. However, EPC population levels dropped again to 60% at 7 days and to 69% 14 days after surgery. This is probably due to a sustained EPC recruitment to the injured area, while EPC regeneration and mobilization are maintained at a static status after an acute active post-injury EPC regeneration period. A similar phenomenon was observed in kidney endothelial injury in mice. Blood EPC levels were increased up to peak on 3 days after kidney endothelial injury and reduced after 5 days post-injury (Hohenstein, B et al., *Nephrology, dialysis, transplantation: official publication of the European Dialysis and Transplant Association-European Renal Association*, 2010; 25:3170-3180).

The data indicates that HHcy suppresses CD34$^+$/VEGFR2$^+$ PC generation in the BM but not in the PB. This is based on the suppression of CD34$^+$/VEGFR2$^+$ PC populations in BM but are unchanged in circulation in HHcy mice with or without GFP CD34$^+$ PC transfusion (FIG. 1C-FIG. 1D, FIG. 3C-FIG. 3D). It is interesting that the suppressed BM CD34$^+$/VEGFR2$^+$ PC generation has no impact on the CD34$^+$/VEGFR2$^+$ population in PB in mice without vascular surgery (FIG. 1C-FIG. 1D), but only associates with the impaired post-injury CD34$^+$/VEGFR2$^+$ PC replenishment in the PB in HHcy mice (FIG. 2F-FIG. 2G).

In HHcy mice, post-injury CD34$^+$/VEGFR2$^+$ PC replenishment is reduced to 40% and 60% 1 day and 3 days post-carotid injury compared with 63% and 88% in the control mice (FIG. 2F-FIG. 2G). In the efforts to identify the origin of post-injury PC replenishment, adaptive PC transfer was applied using BM GFP$^+$/CD34$^+$ cells and it was discovered that BM GFP$^-$/CD34$^+$/VEGFR2$^+$ cells from the recipient mice were completely recovered and increased to 292% 3 days post-injury in the control mice. This replenishment is largely impaired and reduced to 185% in the HHcy mice (FIG. 3C-FIG. 3D). The survival of the transfused GFP$^+$/CD34$^+$ cells is not changed by HHcy and have similar half-lives in the control and HHcy mice (105.78±9.33 hr and 101.47±10.82 hr). These data demonstrate that BM-origin EPCs contribute to post-injury PC replenishment under normal conditions, and that HHcy inhibits post-injury PC replenishment, or post-injury EPC mobilization from the BM.

By using in vivo imaging analysis, strong evidence is provided for active and efficient post-injury circulating EPC homing to the injured area. As shown in FIG. 4B, transfused BM CD34$^+$ cells accumulate at the injured carotid 24 h after surgery and remain concentrated in the injured artery site at day 3 while the majority of the transfused CD34$^+$ cells metabolized in liver and were excreted away from the bladder. As a result of post-injury circulating EPC homing to the injured area, the transfused GFP$^+$/CD34$^+$ cells are engrafted into the injured endothelium and contribute to endothelial repair, which can be identified by en face GFP staining (FIG. 4C). HHcy is demonstrated to suppress GFP$^+$/CD34$^+$ cells engraftment (FIG. 4D, FIG. 4F). The previous finding that HHcy impairs re-endothelialization (Tan, H et al., *Cardiovascular research*, 2006; 69:253-262) was confirmed, and GFP$^+$/CD34$^+$ cell therapy has been discovered to improve post-injury re-endothelialization (FIG. 4E) and vascular remodeling (FIG. 5A-FIG. 5G) in HHcy mice. It was found that BM CD34$^+$ PC transfusion largely improved post-injury re-endothelialization (FIG. 4E) and vascular remodeling in HHcy mice, but had no such effect in control mice. CD34$^+$ PCs have been previously tested for vascular repair and tissue healing in humans and mice, and implicated some therapeutic benefit (Kalka, C., *Proceedings of the National Academy of Sciences of the United States of America*, 2000; 97:3422-3427 and Yang, J et al., *PloS one*, 6:e20219). This study emphasizes that CD34$^+$ PC therapy is beneficial for vascular disease which is characterized for endothelial injury, such as HHcy associated vascular injury (Wang, H et al., *The Journal of biological chemistry*, 1997; 272:25380-25385 and Wang, H et al., *Blood*, 2002; 99:939-945) and organ transplantation, in which endothelial cell death is a major trigger of graft vasculopathy (Koch, A et al., *European journal of cardio-thoracic surgery: official journal of the European Association for Cardio-thoracic Surgery*, 2001; 20:996-1001).

GFP$^+$/CD34$^+$ cell transfusion was observed to improve, but did not completely correct HHcy-impaired post-injury re-endothelialization (FIG. 4E) and vascular remodeling. This may be mostly explained by the inhibitory effect of HHcy on EPC adhesion, migration and proliferation (FIG. 6A-FIG. 6H). A better benefit of post-injury PC therapy may be achieved if PC therapy can be combined with Hcy-lowering strategy or gene-therapy with the correction of targeting genes identified in Hcy signaling.

It is known that cell adhesion molecules (CAMs) play a critical role in the recruitment of circulating PCs in the injured tissues (Duan, H et al., *Thromb Haemost.*, 2006; 96:807-815 and de Boer, H C et al., *Arteriosclerosis, thrombosis, and vascular biology*, 2006; 26:1653-1659). Among 4 types of CAMs (cadherins, Immunoglobulin superfamily (IgSF), selectins, and integrins), integrin is the major CAM mediating cell-ECM interactions (Korta, K, et al., *Postepy Hig Med Dosw (Online)*, 2013; 67:982-995), which is a pathophysiological condition in vascular injury, where endothelium is largely denuded and the sub-endothelial ECM is exposed. 24 different intergrin heterodimers have been identified in higher vertebrates via different combinations of eighteen α- and eight β-subunits. The β1 and αvβ3 integrins have been implicated in mediating EPC adherence and homing to denuded vessels (Walter, D H et al., *Circulation*, 2002; 105:3017-3024 and Kokubo, T et al., *Journal of vascular surgery*, 2007; 45 Suppl A:A33-38). It was found that β1, but not αvβ3, integrin is reduced and inactivated by Hcy in cultured hEPCs (FIG. 6A-FIG. 6H). Hcy-suppressed adhesion (82% of the control) and migration (72% of the control) was rescued using a function-activating anti-β1 integrin antibody (12G10), as it binds to the β1 ligand-induced binding site leading to conformational change and enhancing β1-fibronectin interactions and activity (McIlhenny, S E et al., *Tissue Eng Part A*, 16:245-255 and Ohle, S J et al., *Am J Respir Cell Mol Biol*.). These results demonstrate that β1 integrin suppression mediates Hcy-impaired EPC adhesion and migration, which are largely reversed by antibody-induced β1 activation.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a vascular disease in a subject, the method comprising:
   administering to a subject in need thereof, wherein the subject has a metabolic disorder an effective amount of CD34$^+$/Vascular Endothelial Growth Factor Receptor-2$^+$ (VEGFR2$^+$) bone marrow-derived endothelial progenitor cells (EPCs) to the subject with a metabolic disorder in need thereof,
   wherein the bone marrow-derived EPCs are genetically modified by gene transfer, and
   wherein the gene is DNA Methyltransferase-1 (DNMT1).

2. The method of claim 1, wherein the vascular disease is associated with endothelial injury.

3. The method of claim 1, wherein the vascular disease is hyperhomocysteinemia (HHcy), hyperlipidemia and diabetes associated vascular injury.

4. The method of claim 1, wherein the bone marrow-derived EPCs are enriched for CD34$^+$/VEGFR2$^+$.

5. The method of claim 1, wherein the bone marrow-derived EPCs are modified prior to administration to the subject.

6. The method of claim 1, wherein the bone marrow-derived EPCs are modified during or after administration to the subject.

7. The method of claim 1, wherein the bone marrow-derived EPCs are administered to the subject by at least one of direct injection, venous infusion, and arterial infusion.

8. The method of claim 1, wherein the bone marrow-derived EPCs differentiate into endothelial cells in the subject.

9. The method of claim 1, wherein the subject is also treated, either serially or in parallel, with a combination therapy.

10. The method of claim 9, wherein the combination therapy comprises administering to the subject at least one active agent selected from the group consisting of a therapeutic agent, an anti-angiogenic or anti-vascular agent, an anti-inflammation agent, a VEGF inhibitor, an antibiotic, an anti-viral agent, an anti-fungal agent, an anti-protozoal agents, a hormone, a radioactive agent, a toxin, an anesthetic, and any combinations thereof.

* * * * *

UNITED STATES PATENT AND TRADEMARK OFFICE
CERTIFICATE OF CORRECTION

| | |
|---|---|
| PATENT NO. | : 9,901,639 B2 |
| APPLICATION NO. | : 15/044859 |
| DATED | : February 27, 2018 |
| INVENTOR(S) | : Hong Wang |

It is certified that error appears in the above-identified patent and that said Letters Patent is hereby corrected as shown below:

In the Specification

On Column 1, Line 15, please replace the paragraph titled "STATEMENT REGARDING FEDERALLY SPONSORED RESEARCH OR DEVELOPMENT" with the following paragraph:
--STATEMENT REGARDING FEDERALLY SPONSORED RESEARCH OR DEVELOPMENT
This invention was made with government support under HL077288, HL117654, HL108910, HL067033, HL116917, HL094451, HL082774, and HL110764 awarded by the National Institutes of Health. The government has certain rights in the invention.--

Signed and Sealed this
Twenty-fourth Day of October, 2023

Katherine Kelly Vidal
*Director of the United States Patent and Trademark Office*